United States Patent [19]
Brown et al.

[11] Patent Number: 5,512,545
[45] Date of Patent: Apr. 30, 1996

[54] PDGF-B ANALOGUES

[75] Inventors: David Brown, Canterbury; Richard M. Edwards, Oxford; Stewart Craig, Oxford; Anne L. Cook, Oxford; John M. Clements, Oxford, all of England

[73] Assignee: British Biotech Pharmaceuticals Limited/Pfizer Limited, United Kingdom

[21] Appl. No.: 94,079

[22] PCT Filed: Jan. 24, 1992

[86] PCT No.: PCT/GB92/00141

§ 371 Date: Aug. 31, 1993

§ 102(e) Date: Aug. 31, 1993

[87] PCT Pub. No.: WO92/13073

PCT Pub. Date: Aug. 6, 1992

[30] Foreign Application Priority Data

Jan. 25, 1991 [GB] United Kingdom .................. 9101645

[51] Int. Cl.$^6$ .......................... A61K 38/18; C12N 15/18; C07K 14/475
[52] U.S. Cl. .......................... 514/12; 530/350; 530/399; 435/69.4; 435/252.33; 435/255.1; 435/320.1; 536/23.51
[58] Field of Search .................. 435/69.1, 69.4, 435/172.3, 320.1, 240.2, 252.33, 255.1, 255.2; 530/350.399; 514/2, 8, 12; 536/23.5, 23.51

[56] References Cited

U.S. PATENT DOCUMENTS

| | | | |
|---|---|---|---|
| 4,766,073 | 8/1988 | Murray et al. | 435/172.3 |
| 4,769,328 | 9/1988 | Murray et al. | 435/69.1 |
| 4,801,542 | 1/1989 | Murray et al. | 435/172.3 |
| 4,845,075 | 7/1989 | Murray et al. | 514/12 |

FOREIGN PATENT DOCUMENTS

| | | |
|---|---|---|
| 0259632 | 3/1988 | European Pat. Off. . |
| 0282317 | 9/1988 | European Pat. Off. . |

OTHER PUBLICATIONS

McBride & Caruthers (1983), *Tetrahedron Letters*, vol. 24, pp. 245–248.
Chambers et al. (1989), *Mol. Cell. Biol.*, vol. 9, pp. 5516–5524.
Kunkel et al. (1987), *Methods in Enzymol.*, vol. 154, pp. 367–382.
Clements et al. (1989), *Gene*, vol. 83, pp. 1–14.
Raines et al. (1985), *Methods in Enzymol.*, vol. 109, pp. 749–773.
Berridge et al. (1982), *Biochem. J.*, vol. 206, pp. 587–595.
Khym (1975), *Clin. Chem.*, vol. 21, pp. 1245–1252.
Bone et al. (1984), *Biochem. J.*, vol. 221, pp. 803–811.
Thomas, P. S. (1980), *P.N.A.S.*, vol. 77, pp. 5201–5205.
Laemmli et al. (1970), *Nature*, vol. 227, pp. 680–685.
Vogel et al. (1989), *Biochemistry*, vol. 28, pp. 2961–2966.
King et al. (1985), *Proc. Natl. Acad. Sci. USA*, vol. 82, pp. 5259–5299.
LaRochelle et al. (1990), *Science*, vol. 248, 1541–1544.
Giese et al. (1990), *Mole. Cell. Bio.*, vol. 10, pp. 5496–5501.
Hart et al. (1990), *Biochemistry*, vol. 29(1), pp. 166–172.
Craig et al. (1992), *Biochemical J.*, vol. 281(1), pp. 67–72.
Clements, J. M. et al. (1991), *The EMBO J.*, Vol. 10, (13), pp. 4113–4120.
Cook, A. L. et al. (1992), *Biochemical J.*, vol. 281, pp. 57–65.

*Primary Examiner*—Marianne P. Allen
*Attorney, Agent, or Firm*—Banner & Allegretti, Ltd.

[57] ABSTRACT

PDGF-B analogues are prepared in which an amino acid residue at a protease site is replaced with the corresponding amino acid residue from PDGF-A. The polypeptide is obtained at yields which are five to ten times greater than that for naturally occurring PDGF-B and retains the biological activity of the natural polypeptide.

26 Claims, 9 Drawing Sheets

FIG. 2 (1/2)

```
AGCTTACCTGCTATGTCCTTGGGTTCGTTAACCATGCGCTGAACCGG CTATGATCGCCGA
||||||||||||||||||||||||||||||||||||||||||||||| ||||||||||||
ATGGACGATACAGGAACCCAAGCAATTGGTAGCGACTTGGCCGATACTA GCGGCT

ATGTAAGACGCGGTACCGAAGTTTTCGA AATCTCGAGACGTTTGATTGACCGCACCAACGC
|||||||||||||||||||||||||||| |||||||||||||||||||||||||||||||
TACATTCTGCGCCATGGCTTCAAAAGCTTTAGAGC TCTGCAAACTAACTGGCGTGGTTGCG

CAACTTCCTG GTTTGGCCGCCATGTGTGTTGAAGTCCAACGCTGCAGTGGTTGCT GTAACAA
|||||||||| |||||||||||||||||||||||||||||||||||||||||||| |||||||
GTTGAAGGACCAAACCG GCGGTACACAACTTCAGGTTGCGACGTCACCAACGACATTGTT

CAGAAACGTTCAGTGTGTCGACCTACTCAGGTTCAA CTGCGTCCTGTCCAAGTTCGTAAGAT
|||||||||||||||||||||||||||||||||||| ||||||||||||||||||||||||
GTCTTTGCAAGTCACAGCTGGATGAGTCCAAGTTGACGCAG GACAGGTTCAAGCATTCTA

CGAAATTGTACGTAAGA AACCAATCTTCAAGAAAAGCCACTGTAACTCTAGAAGACCACC T
||||||||||||||||| |||||||||||||||||||||||||||||||||||||||||| |
GCTTTAACATGCATTCTTTGGTTA GAAGTTCTTTCGGTGACATTGAGATCTTCTGGTGGA
```

FIG. 2 (2/2)

```
GGCATGCAAGTGTGAAACTGTTGCAGCTGCTCGCCCTGT TACTAGATCTCCGGGTGGTTC
||||||||||||||||||||||||||||||||||||||| ||||||||||||||||||||
CCGTAC GTTCACACTTTGACAACGTCGACGAGCGGGACAATGATCT AGAGGCCCACCAAG

CCAGGAACAACGCGCTAAAACC CCACAAACCCGGGTTACCATCAGAACTGTTCGCGTCCG
|||||||||||||||||||||| |||||||||||||||||||||||||||||||||||||
GGTCCTTGTTGCGCGATTTTGG GGTGTTT GGGCCCAATGGTAGTCTTGACAAGCGCAGGC

TAG ACCTCCCAAGGGTAAACACCGCAAATTCAAGCACACCCCACGACA AAACCGCTTTAAA
||| |||||||||||||||||||||||||||||||||||||||||||| ||||||||||||
ATCTGGAGGG TTCCCATTTGTGGCGTTTAAGTTCGTGTGGGGTGCTGTTTTGGCG AAATTT

GGAAACCTTAGGTGCTTAGTAAGGATCCG
|||||||||||||||||||||||||||||
CCTTTGGAATCCACGAATCATTCCTAGGCTTAA
```

FIG.3 (1/3)

```
            M   S   L   G   S   L   T   I   A   E   P   A   M   I   A   E
AAGCTTACCTGCTATGTCCTTGGGTTCGTTAACCATCGCTGAACCGGCTATGATCGCCGA
----+----+----+----+----+----+----+----+----+----+----+----+
TTCGAATGGACGATACAGGAACCCAAGCAATTGGTAGCGACTTGGCCGATACTAGCGGCT
         10        .        30        .        50        .

C   K   R   T   E   V   F   E   I   S   R   R   L   I   D   R   T   N   A
ATGTAAGACGCGGTACCGAAGTTTCGAAATCTCGAGACGTTTGATTGACCGCACCAACGC
----+----+----+----+----+----+----+----+----+----+----+----+
TACATTCTGCGCCATGGCTTCAAAGCTTTAGAGCTCTGCAAACTAACTGGCGTGGTTGCG
         .        70        .        90        .        110

N   F   L   V   W   P   P   C   V   E   V   Q   R   C   S   G   C   C   N   N
CAACTTCCTGGTTTGGCCGCCATGTGTTGAAGTCCAACGCTGCAGTGGTTGCTGTAACAA
----+----+----+----+----+----+----+----+----+----+----+----+
GTTGAAGGACCAAACCGGCGGTACACAACTTCAGGTTGCGACGTCACCAACGACATTGTT
         .        130       .        150       .        170

R   N   V   Q   C   R   P   T   Q   V   Q   L   R   P   V   Q   R   K   I
CAGAAACGTTCAGTGTCGACCTACTCAGGTTCAACTGCGTCCTGTCCAAGTTCGTAAGAT
----+----+----+----+----+----+----+----+----+----+----+----+
GTCTTTGCAAGTCACAGCTGGATGAGTCCAAGTTGACGCAGGACAGGTTCAAGCATTCTA
         .        190       .        210       .        230
```

FIG.3 (2/3)

```
  E   I   V   R   K   K   P   I   F   K   K   A   T   V   T   L   E   D   H   L
CGAAATTGTACGTAAGAAGCCAATCTTCAAGAAGCCACTGTAACTCTAGAAGACCACCT
----+----+----+----+----+----+----+----+----+----+----+----+
GCTTTAACATGCATTCTTTGGTTAGAAGTTCTTCGGTGACATTGAGATCTTCTGGTGGA
          250                 270                 290

A   C   K   C   E   T   V   A   A   A   R   P   V   T   R   S   P   G   G   S
GGCATGCAAGTGTGAAAACTGTTGCAGCTGCCCTCGTGTTACTAGATCTCCGGGGTGGTTC
----+----+----+----+----+----+----+----+----+----+----+----+
CCGTACGTTCACACTTTGACAACGTCGACGGGAGCACAATGATCTAGAGGCCCACCAAG
          310                 330                 350

Q   E   Q   R   A   K   T   P   Q   T   R   V   T   I   R   T   V   R   V   R
CCAGGAACAACGCGGCTAAAACGGGCTAAAACCCCACAAACCCGGGTTACCATCAGAACTGTTCGCGTCCG
----+----+----+----+----+----+----+----+----+----+----+----+
GGTCCTTGTTGCGCCGATTTTGCGCCGATTTTGGGTGTTTGGGCCCAATGGTAGTCTTGACAAGCGCAGGC
          370                 390                 410

R   P   P   K   G   K   H   R   K   F   K   H   T   H   D   K   T   A   L   K
TAGACCCTCCCAAGGGTTCCCATTGTGGGCGTTTAAGTTCCGTGTGTGGGTGCTGTTTTGGCGAAATTT
----+----+----+----+----+----+----+----+----+----+----+----+
ATCTGGAGGGTTCCCAAGGGTAACACCGCAAATTCAAGGCACACCCGACAAAACCGCTTTAAA
          430                 450                 470
```

FIG. 3 (3/3)

```
       E   T   L   G   A   *   *
GGAAACCTTAGGTGCTCTTAGTAAGGATCCGAATTC
----+----|----+----|----+----|----+
CCTTTGGAATCCACGAATCATTCCTAGGCTTAAG
         490                510
```

(c)

R  NR (d)

R  NR

PDGF-B ANALOGUES

FIELD OF THE INVENTION

The present invention relates to protease-resistant mutants of the B chain of human platelet-derived growth factor (PDGF).

BACKGROUND OF THE INVENTION

PDGF is a mitogen which is released from the alpha-granules of platelets following activation. The mitogenic activity of this growth factor is restricted to cells of mesothelial origin, glial cells and fibroblasts, but excluding arterial endothelium cells.

PDGF isolated from blood is predominantly a disulphide-linked heterodimer having a molecular weight of 28000–31000 and is composed of two chains, the A chain (PDGF-A) and the B chain (PDGF-B). The mature A and B chains show 60% homology and the 8 cysteine residues in each chain are conserved. The PDGF B chain (SEQ ID NO: 1) is essentially homologous to the v-sis oncogene product, $p28^{sis}$, derived from simian sarcoma virus. The major form of PDGF found in human serum is the heterodimer of the A and B chains, but homodimers are also present in small quantities. Homodimers of PDGF-BB are found in porcine.serum and PDGF-AA is produced by several human tumour cell Lines. The reduced monomeric forms of PDGF are biologically inactive.

PDGF receptors are composed of two sub-units, alpha and beta. The beta-receptor sub-unit can only bind the B chain of PDGF, but the alpha-receptor sub-unit binds both the A and the B chains and therefore it is possible to mediate the different biological functions of PDGF via the isoforms and the porportion of alpha-and beta-receptor sub-units on cells.

There is no structural model of PDGF and the residues responsible for binding to the receptor have not been defined. Circular dichroism measurements have shown a high content of random structure and a low alpha helical content (Vogel and Hoppe 1989, *Biochemistry* 28, 2961–2966). The minimal v-sis transforming domain has been shown to span the 89 residues indentical to PDGF and containing all 8 conserved cysteines (King et al 1985, *P.N.A.S.*, 82, 5259–5299). Chimeras of PDGF-A and B chains have been used to define a region from residues 24–63 (numbering from the mature N-terminus) to be responsible for the transforming ability of PDGF-BB (LaRocheHe et al, 1990, *Science*, 248, 1541–1544). More recently, using single amino acid deletions, the receptor binding domain has been shown to be between residues 25 and 37 from the mature N-terminus. (Giese et al, 1990, *M.C.B.*, 10, 5496–5501).

PDGF has been implicated in a number of diseases involving abnormal cell proliferation, inflammation, fibrosis, atherosclerosis and neoplasia. In addition, PDGF is thought to be an important component of the wound healing process. There is therefore considerable interest in the therapeutic potential of PDGF antagonists and agonists. The production of large quantities of PDGF is therefore desirable and the simplest way to achieve this is by recombinant DNA technology.

Recombinant PDGF is known and has been described in several prior publications for example U.S. Pat. No. 4769328 and U.S. Pat. No. 4801542, describe biologically active PDGF analogues expressed in yeast.

U.S. Pat. No. 4766073 discloses dimetic proteins substantially homologous to the A-chain or the B-chain of PDGF or portions thereof, and an A-B heterodimer, expressed in yeast. In addition a portion of the DNA sequence may encode a portion of the A-chain while another may encode a portion of the B-chain.

U.S. Pat. No. 4845075 discloses dimeric proteins which have substantially the same biological activity as PDGF. The proteins consist of dimers of polypeptides which are substantially homologous to PDGF-B and the specification suggests that it may be advantageous to truncate the protein or to change the amino acid residues. In particular, Cys residues may be substituted by other amino acid residues.

More specifically a truncated form of PDGF is disclosed. The Lys-Arg at the alpha factor B-chain boundary was removed, and it was proposed that proteolytic processing would occur at the internal Arg-Arg site at position 27–28. Mitogenic activity was observed with this construct. No N-terminal sequence analysis or SDS-PAGE analysis was performed on this construct and therefore it is not known at what position the processing took place. It is probable that an alternative site within alpha factor or PDGF-B was used since a molecule not containing the receptor binding region would have very low mitogenic activity.

EP-A-0282317 describes two forms of the PDGF-A chain, and PDGF-A-chain/B-chain heterodimers. The polypeptides were expressed in yeast and produced active PDGF dimers.

However, there is a major problem associated with the production of recombinant DNA which has not been addressed in the prior art and this is that the expression of the PDGF B chain, particularly in yeast, is very low. Yeasts are particularly suitable organisms for the expression of PDGF since, unlike *E. coli*, they contain proteases which allow maturation cleavage of the polypeptide chains. In addition, unlike transformed mammalian cells, they do not contain oncogenes. It would therefore be advantageous to develop a strategy for increasing the yield of recombinant PDGF-B in yeast.

It has previously been shown that both PDGF-A and PDGF-B undergo proteolytic processing during expression and secretion in vivo and that the mature A chain has 104 amino acid residues whilst the mature B chain has 109 amino acid residues.

However, it has been observed that recombinant PDGF is cleaved by proteases not only at the normal matruation site but also at various other sites along the chain an it is probable that this additional cleavage is to a large extent responsible for the low expression of recombinant PDGF-B in yeast. If this cleavage could be eliminated, then it is likely that the expression of PDGF-B would be greatly EP-A-0282317 relates to polypeptides expressed in CHO cells having a sufficient part of the structural conformation of PDGF to bind to monoclonal antibodies specific for epitopes of the B chain of PDGF. N-terminal amino acid sepuence analysis of the recombinant PDGF produced in CHO cells reveals a small percentage of a terminus begining at amino acid 33 Thr-Asn-Ala-Asn-Phe and at amino acid 80 Lys-Lys-Pro-Ile-Phe. Similar processing has been observed. in platelets. These products were reasoned to be due to the action of specific proteolytic enzymes found inside CHO cells and platelets. The authors suggested that the cleavage site residues and adjacent residues may be altered to prevent cleavage.

It has already been demonstrated that it is possible to disrupt the protease cleavage sites of polypeptides or proteins by the substitution of an amino acid residue at the cleavage site with another amino acid residue.

The amino acid at the cleavage site is usually replaced by an amino acid having a similar chemical nature. However, problems can arise with this approach since, on the one hand, it is important to ensure that the cleavage site is actually disrupted whilst on the other hand, the protein must retain its biological activity and it is often difficult to modify the protein in such a way that it meets both of

SUMMARY OF THE INVENTION

The inventors have unexpectedly discovered that a major cleavage site in PDGF-B when expressed in yeast appears to occur between the Arg residue at position 32 and the Thr residue at position 33. It would therefore be desirable to prepare PDGF-B analogues which disrupt this cleavage site. However, this aim is complicated by the fact that the PDGF-B binding region is known to occur in the region between Ilc 25 and Phe 37 and therefore the alteration of residues without affecting binding is likely to present particular problems.

In a first aspect of the present invention therefore there is provided a PDGF-B analogue wherein at least one amino acid residue is replaced by a residue which reduces or prevents cleavage after Arg 32 on expression in yeast and wherein the analogue, when dimerised, has a biological activity at least as great as that of a dimer comprising unmodified PDGF-B.

In a second aspect of the invention there is provided a PDGF-B analogue wherein Arg 28 is replaced by another residue and wherein the analogue, when dimerised, has a biological activity at least as great as that of a naturally occurring PDGF-B dimer.

Preferably Arg 28 is replaced by Ser.

In a third aspect of the invention there is provided a PDGF analogue having the amino acid-sequence of SEQ ID NO 3.

In a further aspect, the invention provides a PDGF-B analogue wherein Arg 32 is replaced by another residue and wherein the analogue, when dimerised, has a biological activity at least as great as that of a naturally occurring PDGF-B dimer. Arg 32 may be replaced by Pro.

In a further aspect, there is provided a PDGF-B analogue having the amino acid sequence of SEQ ID NO 4.

In still another aspect, the invention provides a PDGF-B analogue wherein both Arg 28 and Arg 32 are replaced by other residues and wherein the analogue, when dimerised, has a biological activity at least as great as that of a naturally occurring PDGF dimer.

Arg 28 may be replaced by a non-basic amino acid, preferably by a neutral (for example polar) amino acid such as Ser; and Arg 32 may also be replaced by a non-basic amino acid, preferably by a neutral (for example non-polar) amino acid such as Pro. The conformationally disrupting effects of Pro may be desirable, and so another amino acid which causes disruption may also be preferred.

In a further aspect of the invention there is provided a PDGF-B analogue having the amino acid sequence of SEQ ID NO 5.

In still another aspect of the invention, there is provided a method of increasing the expression in yeast of PDGF-B, comprising substituting one or both of Arg 28 and Arg 32 of the mature PDGF-B chain with another amino acid residue, such that the activity of the PDGF dimer is not materially decreased.

Arg 28 may be replaced by a non-basic ammo acid, preferably by a neutral (for example polar) amino acid such as Ser; and Arg 32 may also be replaced by a non-basic amino acid, preferably by a neutral (for example non-polar) amino acid such as Pro. The conformationally disrupting effects of Pro may be desirable, and so another amino acid which causes disruption may also be preferred.

The common amino acids other than Arg are as follows:

Basic: Lys, His

Acidic: Asp, Glu

Polar: Gly, Ser, Thr, Cys, Tyr, Asn, Gln

Non-polar: Ala, Val, Leu, Ile, Pro, Phe, Trp, Met

Polypeptides with substitutions in accordance with the invention were found to be expressed in yeast at levels which were 5 to 10 times greater than the naturally occurring molecule. It was found that for the mutant in which Arg 32 is replaced by Pro, them was no cleavage of the polypeptide between amino acid residues 32 and 33 whilst for the mutant in which Arg 28 is replaced by Ser, there was only a low level of cleavage between residues 32 and 33. This may be because substitution of the arginine residue alters the accessibility of protease to the cleavage site after Arg 32 resulting in reduced levels of cleavage.

In some cases it may be desirable to incorporate additional modifications into the PDGF-B molecule as well as replacing the residues discussed above.

In a further aspect of the invention there is provided a recombinant or isolated nucleic acid sequence coding for a PDGF-B analogue as described above.

The nucleic acid sequence is preferably recombinant and may comprise a DNA sequence which is preferably incorporated into a vector.

The nucleic acid sequence will preferably have a codon usage optimised for yeast.

In an embodiment of this aspect of the invention there is provided a vector incorporating DNA encoding a PDGF-B analogue.

The vector may be a plasmid, a cosmid or a phage and may be either a cloning vector, for example pUC18, or an expression vector such as one of the yeast expression vectors pSW6 or p/C75. Expression vectors will generally contain a promoter operably linked to the nucleic acid sequence encoding the PDGF-B analogue. Vectors which are not expression vectors are useful as cloning vectors.

In a further aspect of the invention there is provide a host cell comprising a vector incorporating DNA encoding a PDGF-B analogue as previously described.

For the purposes of cloning or manipulation of the DNA sequence, the host cell may comprise *E. coli* or any other suitable organism. For the purposes of expression, the host cell may comprise a yeast which will preferably be *Saccharomyces cerevisiae.*

In another aspect of the invention there is provided a process for the synthesis of PDGF molecules comprising analogues of the B chain, the process comprising coupling together amino acids and/or ligating oligomers.

The coupling of amino acids may involve RNA translation and will usually occur in a host cell which will preferably comprise a yeast such as *Saccharomyces cerevisiae*. The PDGF molecules will be isolated from the culture medium as dimers and therefore if heterodimers of PDGF-AB are required, a gene encoding the A chain may also be incorporated into the host so that co-expression will occur. If both PDGF chains are present, then heterodimers will be formed in preference to homodimers.

In a further aspect of the invention there is provided a process for the preparation of DNA encoding a PDGF-B analogue, the process comprising the coupling together of nucleotides and/or ligating oligonucleotides.

The DNA preparation process will preferably occur in a suitable host cell which may, for example, be E. coli or a similar organism if manipulation or cloning of the DNA is required or, alternatively a yeast such as Saccharomyces cerevisiae if the DNA is to be replicated for the purposes of expression.

In still another aspect of the invention there is provided a process for the preparation of a host cell, the process comprising transfecting the host cell with a vector comprising a nucleotide sequence encoding a PDGF-B analogue as described above.

In yet a further aspect of the invention there is provided a PDGF dimer for use in veterinary or, preferably, human medicine, the dimer comprising at least one PDGF-B analogue as previously described.

In a further aspect of the invention there is provided a PDGF dimer as described above for use in the preparation of a medicament for the promotion of wound healing and/or the treatment of atherosclerosis. The invention may therefore be used in a method of promotion of wound healing and/or in a method of treatment of atherosclerosis. The dose of PDGF dimer to be administered will be likely to vary from patient to patient and will be determined by the physician. As a guideline, a dose of about 0.01 to 10 mg/kg of body weight may be administered.

In another aspect of the invention there is provided a pharmaceutical composition containing at least one PDGF dimer as described above and a pharmaceutically or veterinarily acceptable carrier therefor.

The composition may be adapted for parenteral administration and may therefore be sterile. An example of such a composition would be PDGF dimers in isotonic physiological saline and/or buffer. Alternatively, the composition may be adapted for buccal administration and may be formulated as a pastille or for dermal or transdermal administration in which case it may comprise a cream or ointment or may be incorporated into a transdermal patch.

BRIEF DESCRIPTIONS OF THE DRAWINGS

The invention will now be further described with reference to the following examples and comparative examples and to the drawings in which:

FIG. 2 represents the oligonucleotides used to build a synthetic PDGF-B gene;

FIG. 3 represents the PDGF-B synthetic gene with the amino acid sequence shown above the DNA sequence;

Figure 4:
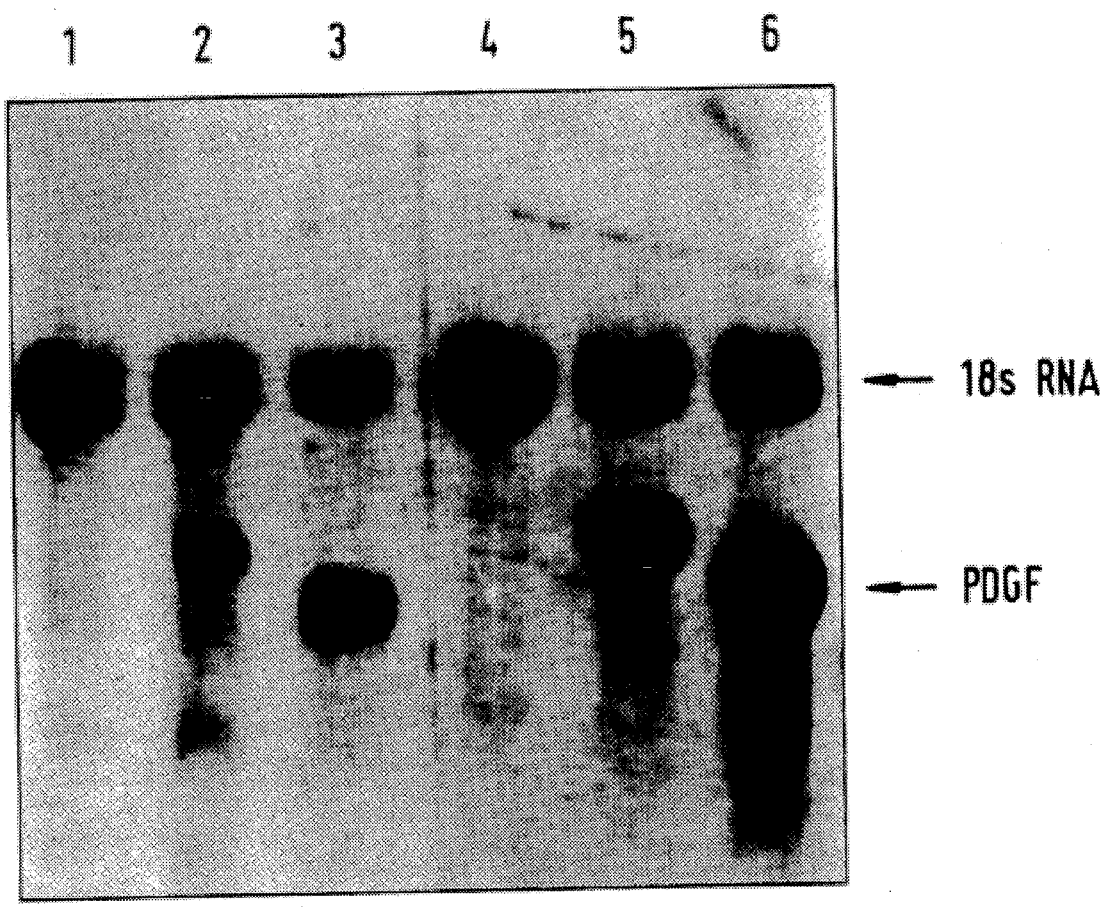
Figure 5A:
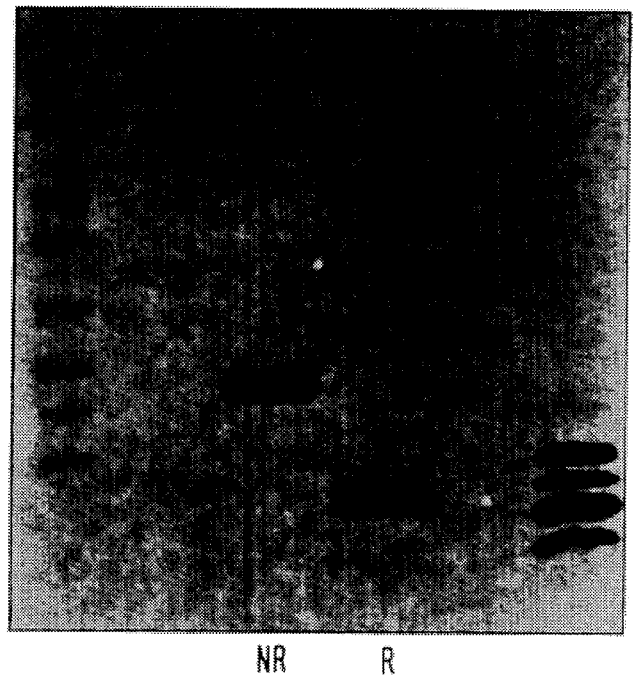
Figure 5B:
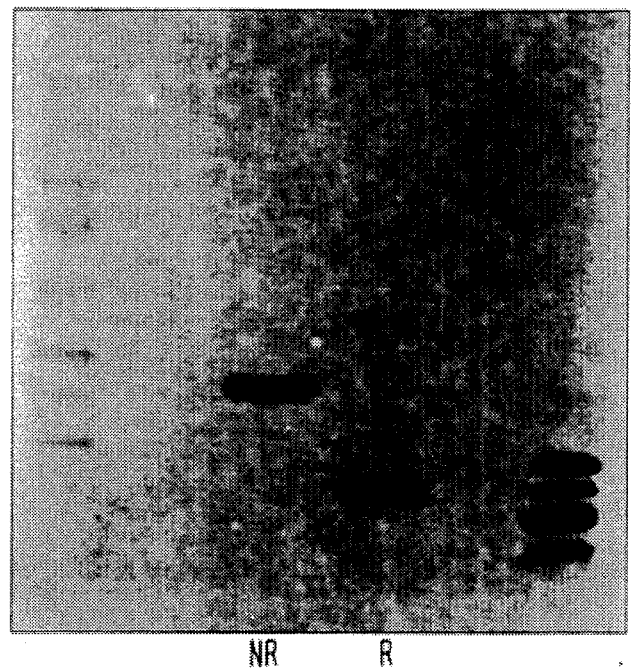
Figure 5C:
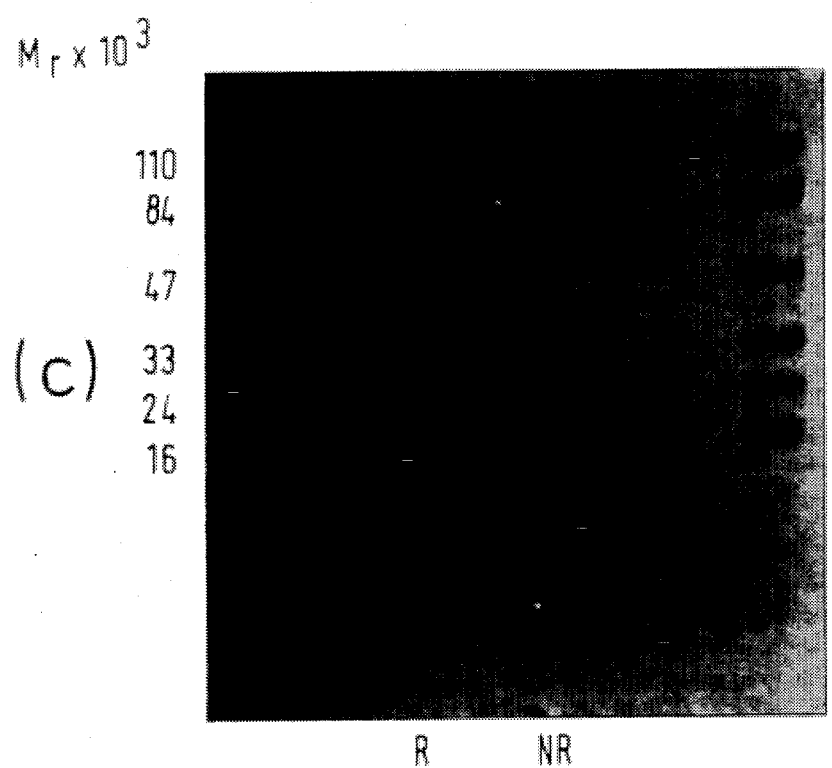
Figure 5D:
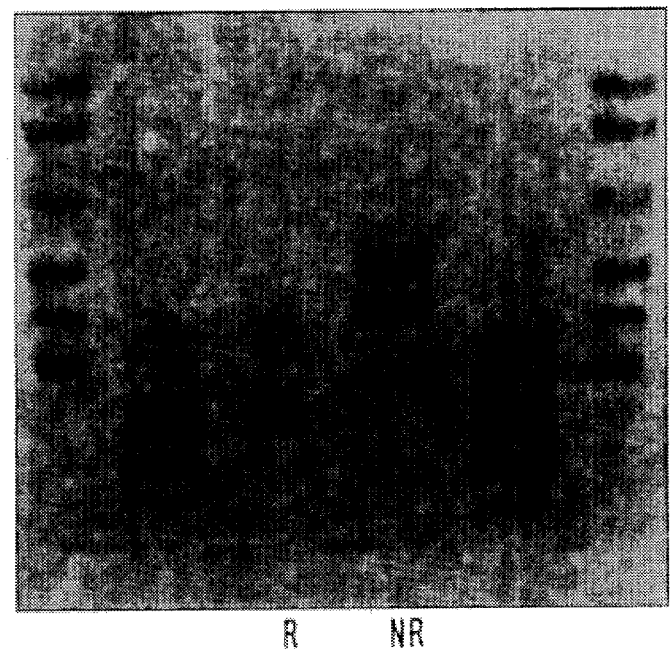

FIG. 4 shows a transcript analysis of PDGF-B and PDGF-Bt: [pSW6 (lanes 1, 4), pSW6/PDGF-B (1-160) (lanes 2, 5) and pSW6/PDGF-B (1-109) (lanes 3, 6) were grown in SC 1% glucose; the cells were harvested and transferred to SC 1% galactose and grown for 16 hours; RNA was prepared from the yeast grown in glucose (lanes 1–3) and galactose (lanes 14); the RNA was analysed by northern blotting using $^{32}$P-labelled oligonucleotides complementary to the synthetic PDGFB gene mRNA and, as an internal loading standard, to the yeast 18S mRNA]; and FIGS. 5a, 5b, 5c and 5d show audioradiographs of Coomassie Blue stained PDGF-B separated by SDS-PAGE. PDGF-B was purified from the yeast supernatant of Examples 1 and 2 and Comparative Example B. [Purified PDGF-BB (FIG. 5a), mutant B5 (FIG. 5b) or mutant B7 (FIG. 5c) were separated by SDS-PAGE on 8–25% PHAST™ gels, under non-reducing (NR) or reducing (R) conditions. $M_r$ standards were in the range 110,000–16,000 and 16,900–6,200. PDGF-BB is cleaved after Arg$_{32}$ and appears as a doublet under reducing conditions. c-sis (Amersham) was analysed under-similar conditions (FIG. 5d) and appears heterogeneous under both non-reducing and reducing conditions.

DETAILED DESCRIPTION OF THE INVENTION

Comparative Example A—Naturally Occuring PDGF-B

Construction of a PDGF-BB Gene

The techniques of genetic engineering and genetic manipulation used in the manufacture of a synthetic PDGF-B gene and in its further manipulation for construction of a yeast expression vector are well known to those skilled in the art. Descriptions of modem techniques can be found in the laboratory manuals "Current Protocols in Molecular Biology" published by Wiley Interscience and in "Molecular Cloning, A Laboratory Manual" (second addition) edited by Sambrook, Fritsch and Maniatis published by Cold Spring Harbour Laboratories, N.Y.

a. Gene Design

A synthetic PDGF-B gene was designed incorporating useful unique restriction sites to facilitate manipulation (see FIG. 3 and SEQ ID NO 6). The selected codons are favoured by either S. cerevisiae or E. coli and are thus suitable for expression in either organism.

b. Gene Construction

The gene sequence was divided into 24 oligodeoxyribonucleotides (See FIG. 2). Each oligonucleotide overlapped its adjacent partner by 7 base pairs, thus providing a cohesive end after annealing of complementary pain of oligonucleotides.

c. Oligonucleotide Synthesis

The oligonucleotides were synthesised by automated phosphoramidite chemistry on an Applied Systems 380B DNA synthesiser, using cyanoethyl phosphoramidites. The methodology is now widely used and has already been described (Beaucage, and Caruthers Tetrahedron Letters, 24, 245 (1981). The oligonucleotides were deprotected and removed from the CPG support by incubation in concentrated NH$_3$. Typically, 50 mg of CPG carrying 1 micromole of oligonucleotide was deprotected by incubation for 5 hours at 70° C. in 600 μl of of concentrated NH$_3$. The supernatant was transferred to a fresh tube and the oligomer precipitated with 3 volumes of ethanol. Following centrifugation the pellet was dried and resuspended in 1 ml of water. The concentration of crude oligomer was then determined by measuring the absorbance at 26 nm.

For gel purification, 10 absorbance units of the crude oligonucleotide was dried down and resuspended in 15/μl of marker dye (90% deionised formamide, 10 mM Tris, 10 mM borate, 1 mM EDTA, 0,1% bromophenol blue). The samples were heated at 90° C. for 1 minute and then loaded onto a 1.2 mm thick denaturing polyacrylamide gel with 1.6 mm wide slots. The gel was prepared from a stock of 15% acrylamide, 0.6% bisacrylamide and 7M urea in 1 X TBE (90mM Tris-borate, pH 8.3, 2. mM EDTA) and was polymerised with 0.1% ammonium persulphate and 0.025% TEMED. The gel was pre-run for 1 hour. The samples were run at 1500 V for 4 to 5 hours. The bands were visualised by UV shadowing and those corresponding to the full length product cut out and transferred to micro-test tubes. The oligomers were eluted from the gel slice by soaking in AGEB (0.5 M ammonium acetate, 0.01M magnesium acetate and 0.1% SDS) overnight. The AGEB buffer was then transferred to fresh tubes and the oligomer precipitated with three volumes of ethanol at −70° C. for 15 minutes. The precipitate was collected by centrifugation in an EPPENDORF microfuge for 10 minutes, the pellet washed in 80% ethanol, the purified oligomer dried, redissolved in 1 ml of water and finally filtered through a 0.45 micron micro filter. The concentration of purified product was measured by determining its absorbance at 260 nm. (The word EPPENDORF is a trade mark).

d. Gene Assembly

The oligonucleotides were kinased to provide them with a 5' phosphate thus enabling subsequent ligation.

Kinasing of Oligomers 100 pmole of oligomer was dried down and resuspended in 20 µl kinase buffer (70 mM Tris, pH 7.6, 10mM $MgCl_2$, 1 mM ATP, 0.2 mM spermidine, 0.5 mM dithiothreitol). 10 µl of T4 polynucleotide kinase was added and the mixture was incubated at 37° C. for 30 minutes. The kinase was then inactivated by heating at 70° C. for 10 minutes.

Complementary pairs of kinased oligonucleotides were annealed in pairs (90° C., 5 minutes, followed by slow cooling). The 12 paired oligomers were then mixed together, incubated at 50° C. for 5 minutes and flowed to cool. They were then ligated overnight at 16° C. with T4 DNA ligase. The oligomers at the ends of the sequence were not kinased to prevent multimerisation. The sequences of the oligomers correspond to those given in FIG. 2.

The ligation products were separated on a 2% low gelling temperature agarose gel and the band corresponding to the PDGF-B gene was excised and extracted from the gel. The purified fragment was then ligated to HindIII-EcoRI treated pUG18 plasmid DNA. (pUG18, code no 27-4949-431, was purchased from Pharmacia Ltd, Midsummer Boulevard, Central Milton Keynes, Bucks, MK9 3HP, United Kingdom.) The transformation of E. coli host strains was accomplished using standard procedures. The strain used as a recipient in the cloning using plasmid vectors was HW87 which has the following genotype:

araD139(ara-leu)Δ7697 (lacIPOZY)Δ74 galU galK hsdR rpsL srl recA56

The use of HW87 was not critical; any suitable recipient strain could be used, for example, E. coli AG1 which is available from Northumbria Biochemicals Ltd.

The recombinant pUC 18 PDGF-B product was transferred into E. coli host strain HW87 and plated onto L-broth ampicillin plates. Twelve colonies were picked and used to prepare plasmid DNA for sequence analysis. Double stranded dideoxy sequence analysis was used to identify a correct clone using a universal sequencing primer (SEQ ID NO 7) CAGGGTTTCCCAGTCACG complementary to the universal primer region of pUC18. The pUC18 recombinant was used to construct the expression vector.

Construction of PDGF-B Expression Vectors

An expression vector was designed to enable the secretion of PDGF-B to the extracellular medium after expression in S. cerevisiae. Secretion of PDGF-B is desirable to facilitate production of protein with an authentic N-terminus, to ease purification, to limit intracellular proteolysis, to reduce potential toxic effects on the yeast host and to allow optimal protein folding via formation of native disulphide bonds. Secretion of PDGF-B through the yeast membrane was directed by fusion of PDGF-B to the yeast mating type alpha-factor pre-pro-peptide (a naturally secreted yeast peptide).

Figure 1:
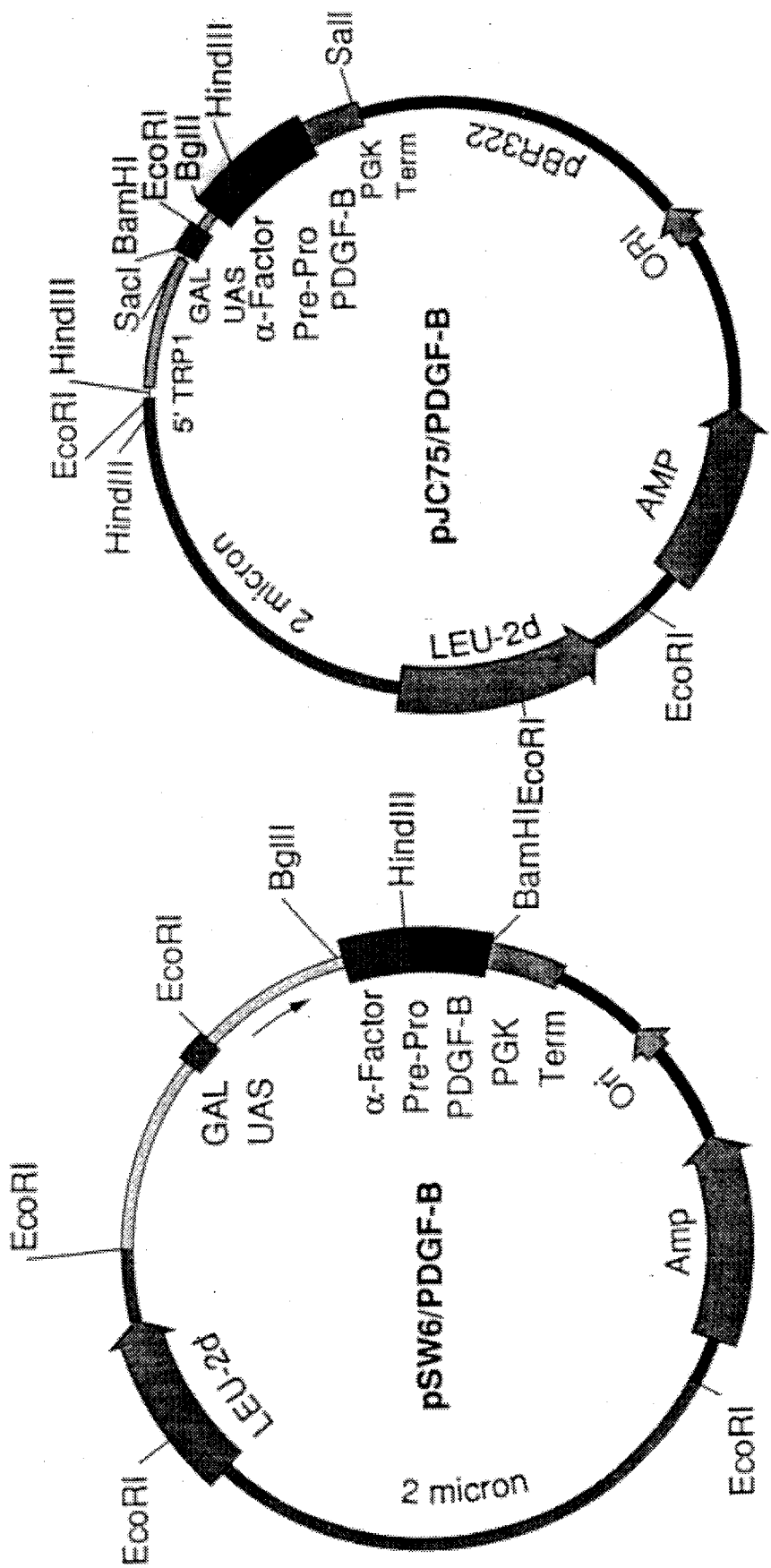
FIG. 1 is a plasmid map of plasmids pSW6/PDGF-B and pJC75/PDGF-B.

The yeast expression vector pSW6 (FIG. 1) is based on the 2 micron circle from S. cerevisiae. (pSW6 was deposited in S. cerevisiae strain BJ2168 at The National Collections of Industrial and Marine Bacteria Limited, 23 Street, Machar Drive, Aberdeen, AB2 1RY, Scotland, United Kingdom on Oct. 23, 1990 under Accession No NCIMB 40326.) pSW6 is a shuttle vector capable of replication in both E. coli and S. cerevisiae and contains a origin of replication for both organisms, the leu2-d gene (a selectable marker for maintenance in the yeast host) and the ampicillin resistant locus for selection of plasmid maintenance in E. coli. (The DNA sequence of the vector has been determined, the E. coli sequences are derived from the E. coli ColE1-based replicon pAT153.) The ability to passage this vector through E. coli greatly facilitates genetic manipulation on this vector. pSW6 contains an alpha-factor pre-pro peptide fused in-frame to epidermal growth factor (EGF). The expression of this fusion is under the control of an efficient galactose regulated promoter which contains hybrid DNA sequences from the S. cerevisiae GAL 1–10 promoter and the S. cerevisiae phosphoglycerate kinase (PGK) promoter. Transcription is terminated in this vector by the natural yeast PGK terminator. The EGF gene in pSW6 can be removed by digestion with HindIII and BamHI. This removes DNA encoding both EGF and 5 amino acids from the C-terminus of the alpha-factor pro-peptide. Genes to be inserted into the pSW6 expression vector must therefore have the general composition: HindIII site alpha-factor adapter—gene—BamHI site.

To rebuild the DNA encoding the 5 amino acids at the C-terminal end of the alpha factor pro-peptide and to fuse this to the synthetic PDGF-B gene, an oligonucleotide adapter 5'AGCTTGGATAAAGATCCTrGGGTTCGTT 3' top strand (SEQ ID NO 8) 5'AACGAACCCAAG- GATCTTTTATCCA 3' bottom strand (SEQ ID NO 9) containing a HindIII site and codons encoding the Ser, Leu, Asp, Lys and Arg from the C-terminal end of the alpha factor adaptor was ligated to the synthetic PDGF-B gene such that the recombinant gene encoded a frame alpha-factor pro-peptide fusion to PDGF-B. The pUC18 PDGF-B plasmid was first cleaved with HpaI to create a blunt ended linear DNA fragment. This fragment was then cut with HindIII and separated on a 1% low gelling temperature agarose gel, excised and extracted from the agarose gel matrix. The fragment was then ligated to the alpha-factor adaptor (synthesised as two complementary oligonucleotides described above) and annealed prior to ligation. The resultant recombinant plasmid was pLF6, the sequence of the HindIII to EcoRI fragment is given in SEQ.ID 10. The alpha-factor adaptor—PDGF-B sequence was removed from pLF6 on a HindIII-BamHI fragment. The fragment was purified on a 1% low gelling temperature agarose gel and ligated to HindIII-BamHI treated pSW6 to create pSW6/PDGF-B. This plasmid is the basic vector used for wild-type PDGF-B expression.

Improved expression was observed using the expression vector pPE280. The pPE280 vector was as described by Chambers, Tsang, Startway, Kingsman & Kingsman, (1989) Mol. Cell. Biol, 9, 5516–5524, with the following exceptions. The 140 base pair GAL1-10 UAS RsaI-AluI fragment from pSW6 was cloned into the BamHI site of pKV560. The interferon sequences at the BglII site were replaced by the alpha-factor PDGF-B fusion on a BglII, BamHI fragment from pSW6/PDGF-B 1–109 (Comparative Example B) to create pJC75 and pSW6/PDGF-B5 to create PJC75/B5.

Expression of PDGF-B Synthetic Gene

Plasmid expression vector pSW6/PDGF-B was transformed into yeast (*S. cerevisiae*) strain BJ12168 (prc-1-407, prb1-1122 pep4-3 leu2 trp 1 ura3- 52 cir+) using the method of Sherman F. et al (Methods in Yeast Genetics, Cold Spring Harbour Laboratory, (1986)). All yeast media was as described by Sherman et al. Using 500 ml baffled flasks, cultures of yeast containing pSW6/PDGF-B were grown in 100 ml batches of 0.67% synthetic complete medium yeast nitrogen base, with amino acids minus leucine and 1% glucose as a carbon source. After overnight growth at 30° C., the cells were harvested by centrifugation at 3000 rpm for 5 minutes and resuspended in the same synthetic complete medium except having 1% galactose and 0.2% glucose as the carbon source. This induces expression from the hybrid PGK promoter. Cells were grown in the induction medium for 6 days. After this period the supernatant was harvested and assayed as described below.

COMPARATIVE EXAMPLE B—Truncated PDGF-B (PDGF-Bt)

PDGF-B was altered to delete the basic 59 amino acid C-terminal extension (SEQ ID NO: 2). The strategy for modification is described below.

Host strains

RZ1032 is a derivative of *E. coli* that lacks two enzymes of DNA metabolism: (a) dUTPase (dut) which results in a high concentration of intracellular dUTP, and uracil N-glycosylase (ung) which is responsible for removing mis-incorporated uracils from DNA (Kunkel et al, *Methods in Enzymol*, 154, 367–382 (1987). A suitable alternative strain is CJ236 available from Bio-Rad Labs, Caxton Way, Watford Business Park, Watford, WD 1 8RP. The principal benefit is that these mutations lead to a higher frequency of mutants in site directed mutagenesis. RZ1032 has the following genotype:

HfrKL16PO/45[lysA961-62), dut1, ung1, thi1, recA, Zbd-279:Tn10, SupE44

JM103 is a standard recipient strain for manipulations involving M13 based vectors. The genotype of JM103 is JM103 Δ (lac-pro), thi, supE, strA, endA, sbcB15, hspR4, F' traD36, proAB, lacIq, ZΔM15.

Site Directed Mutagenesis

Kinased mutagenesis primer (2.5 pmole) was annealed to the single stranded template DNA, which was prepared using Rz1032 as host, (1 μg) in a final reaction mix of 10 μl containing 70 mM Tris, 10 mM MgCl$_2$. The reaction mixture in a polypropylene micro-test tube (Eppendorf) was placed in a beaker containing 250 ml of water at 70° C. for 3 minutes followed by 37° C. for 30 minutes. The annealed mixture was then placed on ice and the following reagents added: 4 μl of 10 X ffM (200 mM HEPES, 100 mM MgCl$_2$ pH 7.6), 5 μl of a mixture of all 4 deoxyribonucleotide triphosphates each at 5 mM, 5 μl of ATP (10 mM), 5 μl DTT, 2 μl of T4 DNA ligase (100 u), 1.0 μl Klenow fragment of DNA polymerase and water to a final volume of 50 μl. The polymerase reaction mixture was then incubated at 15° C. for 4–16 hrs. After the reaction was complete, 150 μl of TE (mM Tris, 1 mM EDTA pH 8.0) was added and the mutagenesis mixture stored at −20° C.

For the isolation of mutant clones the mixture was then transformed into the recipient JM103 as follows. A 5 ml overnight culture of JM103 in 2 X YT (1.6% BACTOTRYPTONE™, 1% Yeast Extract, 1% NaCl) was diluted 1 in a 100 into 50 ml of pre-warmed 2 X YT. The culture was grown at 37° C. with aeration until the A600 reached 0.4. The cells were pelleted and resuspended in 0.5 vol of 50 mM CaCl$_2$ and kept on ice for 15 minutes. The cells were then re-pelleted at 4 ° C. and resuspended in 2.5 ml cold 50 mM CaCl$_2$. For the transfection, 0.25, 1, 2, 5, 20 and 50 μl aliquots of the mutagenesis mixture were added to 200 μl of competent cells which were kept on ice for 30 minutes. The cells were then heat shocked at 42° C. for 2 minutes. To each tube was then added 3.5 ml of YT soft agar containing 0.2 ml of a late exponential culture of JM103, the contents were mixed briefly and then poured onto the surface of a pre-warmed plate containing 2 X YT solidified with 1.5% agar. The soft agar layer was allowed to set and the plates then incubated at 37° C. overnight.

Single stranded DNA was then prepared from isolated clones as follows: single plaques were picked into 4 ml of 2 X YT that had been seeded with 10 μl of a fresh overnight culture of JM103 in 2 X YT. The culture was shaken vigorously for 6 hrs. 0.5 ml of the culture was then removed and added to 0.5 ml of 50% glycerol to give a reference stock that was stored at −20° C. The remaining culture was centrifuged to remove the cells and 1 ml of supernatant carrying the phage particles was transferred to a fresh Eppendorf tube. 250 μl of 20% EPG6000, 250mM NaCl was then added, mixed and the tubes incubated on ice for 15 minutes. The phages were then pelleted at 10,000 rpm for 10 minutes, the supernatant discarded and the tubes re-centrifuged to collect the final traces of PEG solution which could then be removed and discarded. The phage pellet was thoroughly resuspended in 200 μl of TEN (10 mM Tris, 1 mM EDTA, 0.3M NaOAc). The DNA was isolated by extraction with an equal volume of Tris saturated phenol. The phases were separated by a brief centrifugation and the aqueous phase transferred to a clean tube. The DNA was re-extracted with a mixture of 100 μl of phenol, 100 μl chloroform and the phases again separated by centrifugation. Traces of phenol were removed by three subsequent extractions with choloroform and the DNA finally isolated by precipitation with 2.5 volumes of ethanol at −20° C. overnight. The DNA was pelleted at 10,000 rpm for 10 minutes, washed in 70% ethanol, dried and finally resuspended in 50 μl of TE.

A truncated PDGF-B gene constructed by oligonucleotide directed mutagenesis. The PDGF-B gene of Comparative Example A was first transferred into M13 mp19 on a HindIII-BamHI DNA fragment. The oligonucleotide 5'ATCCTTACTA AGTAACAGGG 3' (SEQ ID NO 11) was used to direct the mutagenesis. Clones carrying the desired mutation were identified by DNA sequence analysis. The entire clone was sequenced to ensure that no other mutation had inadvertently been introduced. The sequence of the truncated PDGF-B gene from the HindIII to BamHI sites is given as SEQ ID NO 12. After confirmation of the correct DNA sequence on single stranded templates, replicative form DNA of one mutant was prepared and the DNA encoding the PDGF-B truncated gene was removed on a HindIII-BamHI fragment. The fragment was gel purified and ligated to HindIII-BamHI treated pSW6 thus replacing the EGF gene in pSW6 to create pSW6/PDGF-Bt. pSW6/PDGF-Bt was transformed first into *E. coli* host HW87 and characterised by restriction digestion. A 50ml plasmid preparation was prepared and used to transform yeast strain BJ2168.

The procedure of Comparative Example A was followed for expression of PDGF-Bt.

Transcript analysis of PDGF-B and PDGF-Bt expression

To ensure that transcription was not a limiting factor to PDGF expression in yeast and to demonstrate that PDGF transcripts were being induced in galactose an analysis of the transcripts by Northern blotting was performed. RNA was prepared from yeast strains grown in glucose (uninduced) or in galactose (induced) as described Clements et al (1989), Gene, 83, 1–14. 10ml of yeast culture was centrifuged at 3000 rpm in a bench top centrifuge, the cells harvested and resuspended in 1 ml of lysis buffer (0.1M Nacl, 0.1M Tris HCl pH 9.0, 1 mM Na,EDTA, 0.5% SDS). 1 g of glass beads was added and 1 ml of phenol reagent (phenol/chloroform/isoamyl alcohol, 24:24:1 ) cells were vortexed four times, each for 15 seconds with intervals of 1 minute on ice. The mixture was centrifuged in a microfuge, and the supernatant extracted twice more with phenol reagent. The supernatant was ethanol precipitated, and resuspended in 25 µl of water. Total RNA was separated in a 1.5% agarose gel containing formaldehyde and transferred to a nitrocellulose filter as described by Thomas P. S., 1980, P.N.A.S, 81, 701–704. The filter was baked at 80° C.

To detect the PDGF transcripts, a gamma-$^{32}$P labelled oligonucleotide complementary to the PDGF transcripts was used: 5'CGAGATTTCGAAAACTTCGG-TACGCGTCTTACATTCGGCG 3' (SEQ ID NO 13). As an internal standard to control for the concentration of the RNA in each lane of the filter a gamma-$^{32}$P labelled oligonucleotide complementary to the yeast 18s RNA was used: 5'TGATCCITCCGCAGGTTCACCTACGGAAAC 3' (SEQ ID NO 14). 3pM of each oligonucleotide was labelled with gamma-$^{32}$P to a specific activity of 109 dpm/µg. Hybridizations were carried out essentially as described by Thomas, 1980, P.N.A.S., 81, 701–704. Filters were pre-hybridized at 42 ° C. for 4 to 20 hrs in 10ml hybridization buffer (50% formamide, 50mM PO$_4$ buffer pH6.5, 0.75M NaCl, 0.075M sodium citrate, 100 µg/ml denatured salmon sperm DNA), 0.02% Bovine Serum Albumin, 0.02% polyvinylpyrrolidone 0.02% FICOLL 400. (The word FICOLL is a trade mark.) To 10 ml fresh hybridization buffer was added the PDGF probe at a concentration of 1×106 cpm per ml of hybridization buffer. The fibosomal probe was added at a concentration of 2×104 cpm per ml of hybridization buffer and diluted with 3 pM/ml of the same unlabelled oligonucleotide. The filter was hybridized at room temperature overnight. The filter was then washed 6 times with 200 ml 0.9M NaCl, 0.09M sodium nitrate, 0.1% SDS for 10 minutes each. The filter was then autoradiographed overnight (see FIG. 4).

Comparative Example C—Construction and Expression of PDGF-B4

PDGF-B4 is a PDGF-Bt derivative in which the Arg at coding position 27 has been altered to a Glu. The M13 clone containing PDGF-Bt on a HindIII-BamHI fragment was used as the template for the mutagenesis reaction. The procedure of Comparative Example B was used except that the primer used for mutagenesis was the primer 5'TCAAACGTTCCGAGATTTC 3' (SEQ ID NO 15).

Comparative Example D—Construction and Expression of PDGF-B6

PDGF-B6 is a PDGF-Bt derivative in which the Asp at coding position 31 has been altered to an Arg. The M13 clone containing PDGF-Bt on a HindIII-BamHI fragment was used as the template for the mutagenesis reaction. The procedure of Comparative Example B was used except that the prima used for mutagenesis was the prima 5'TTGGT-GCGCTTAATCAAAC 3' (SEQ ID NO 16).

Example 1—Construction and Expression of PDGF-B5

PDGF-B5 is a PDGF-Bt derivative in which the Arg at coding position 28 has been altered to a Ser, the same residue as found in PDGF-A. The M13 clone containing PDGF-Bt on a HindIII-BamHI fragment was used as the template for the mutagenesis reaction. The procedure of Comparative Example B was used for mutagenesis except that primer was 5'CAATCAAGGATCTCGAGAT 3' (SEQ ID NO 17) and the gene had the sequence shown as SEQ ID NO 18. The amino acid sequence of PDGF-B5 is shown as SEQ ID NO 3.

Example 2—Construction and Expression of PDGF-B7

PDGF-B7 is a PDGF-Bt derivative in which the Arg at coding position 32 has been altered to a Pro, the same residue as found in PDGF-A. The M13 clone containing PDGF-Bt on a HindIII-BamHI fragment was used as the template for the mutagenesis reaction. The procedure of Comparative Example B was for use for mutagenesis except that the primer was 5'GCGTrGGTTGGGTCAATC 3' (SEQ ID NO 19) and the gene had the sequence shown in SEQ ID NO 20. The amino acid sequence of PDGF-B7 is shown as SEQ ID NO 4.

Example 3—Construction and Expression of PDGF-B44

PDGF-B44 is a PDGF-B5 derivative in which the Arg at coding position 32 has been altered to a Pro, the same residue as found in PDGF-A. The M13 clone containing PDGF-B5 on a HindIII-BamHI fragment made as described in Example 1 was used as the template for the mutagenesis reaction. The procedure of Comparative Example B was used except that the primer used for mutagenesis was the primer 5'GCGTTGGTTGGGTCAATC 3 (SEQ ID NO 21) and the gene had the sequence shown as SEQ ID NO 22. The amino acid sequence of PDGF-44 is shown as SEQ ID NO 5.

Analysis of expression

To measure intracellular and extracelluar concentrations of PDGF-B, PDGF-B5 and PDGF-B7 during expression, cultures of each clone were induced over a 6 day period as described in Comparative Example A. Samples were taken on each day from the culture medium, cell wall, and intracellular concentrations of PDGF, 10 ml of cells were centrifuged and resuspended in 0.5 ml 0.9M sorbitol, 20M EDTA, 50 mM beta-mercaptoethanol, 20 µl 100 mg/ml ZYMOLYASE 20T (Seikagaku Kogyo Ltd). (The expression ZYMOLYASE 20T is a trade mark). The cells were incubated at 30° C. for one hour, then centrifuged and the supernatant removed and assayed by ELISA for the PDGF-B concentration in the yeast cell wall. The cells were washed in 1 ml 1M sorbitol, and collected by centrifugation. To lyse the cells, the pellet was resuspended vigorously in 100 mM Tris-HCl pH 7.5, 100mM NaCl, 0.1 % SDS, and lysis was monitored under the microscope. The debris was removed by centrifugation and the supernatant assayed by F-LISA for the intracellular concentration of PDGF-B.

Purification of PDGF-B

Yeast supernatant (5–6 liters was clarified by centrifugation at 8,600 g for 20 minutes at 4° C. The pH was adjusted to 6.0 with 20rnM Tris prior to 5–10 fold concentration by tangential flow ultrafiltration (MILLIPORE MINITAN, PTGC membranes, 10,000 cutoff). (The expression MILLI- PORE MINITAN is a trade mark.) The molarity of the concentrated supernatant was adjusted to 0.09M with NaCl before chromatography using a 200 ml CM SEPHAROSE column (Pharmacia, 5cm×10cm). (The word SEPHAROSE is a trade mark.) The column was washed with 2–3 volumes of 0.19M NaCl and 20 mlVl Tris pH 6.0 and material containing PDGF-B was eluted with 1M NaCl to a 20 ml phenyl SEPHAROSE column (Pharmacia, 1.6 cm×10 cm) equilibrated in the same buffer, followed by washing with 60 ml of 1M NaCl and 20mM Tris pH 7.4 PDGF-B was eluted with 40–60 ml of 50% ethylene glycol, 0.15M NaCl and 20mM Tris pH 7.4. Fractions containing PDGF, assessed by ELISA or mitogenic assay, were pooled and stored at $-200°$ C. for up to 3 months.

Gel filtration chromatography

For measurement of protein by absorbance at 280 nm and N-terminal sequencing, PDGF was transferred from Phenyl SEPHAROSE elution buffer (containing 50% ethylene glycol) into 10 mM acetic acid using a two-step size exclusion chromatography process. The first gel filtration step, using a 250 ml SEPHADEX G-25M column (Pharmacia, 5cm× 12.5cm) transfers PDGF into 0.5M urea and 10mM glycine pH 3.0. (The word SEPHADEX is a trade mark). Protein fractions from this column were pooled and applied to a further 250 ml SEPHADEX G-25M gel filtration column and eluted with 10mM acetic acid. Fractions containing PDGFB were pooled, concentrated by lyophilsation and stored at $-200°$ C.

SDS-PAGE

Chromatography samples were dialysed against 0.1% SDS or transfereed in 10mM acetic acid and lyophilised prior to analysis by SDS-PAGE. Electrophoresis (BioRad MINI PROTEAN system) was performed using 4% stacking gels and 15% separating gels at 200 V for approximately 45 minutes (Laemmli, (1970), *Nature*, 227, 680–685). CYhc expression BioRad MINI-PROTEAN is a trade mark). Analytical samples were separated on 8–25% Phast gels (Pharmacia), under either non-reducing or reducing (with 0,7 M 2-mercaptoethanol) conditions. (The word PHAST is a trade mark). Protein was visualised using either Coomassie Brilliant Blue R250 (BDH) or a silver staining technique (See et al, (1989) *Protein Structure, A practical approach*, Ed T. E. Creighton, I.R.L. Press).

Western Blotting

Electrophoresis was performed as described in the previous section and separated proteins transferred onto nitrocellulose sheets by the method of Towbin, at 100 bolts for one hour (BioRad MINI-PROTEAN TransBlot System). (The expression BioRad MINI-PROTEAN TransBlot is a trade mark). Non-specific binding was blocked by incubation of the nitrocellulose sheets with 2% bovine serum albumin and phosphate-buffered saline (PBS, Dulbecco A, Oxoid) for 16 hours at 4° C. PDGF was detected by incubation with a 1/200 dilution of rabbit anti-human PDGF antibody CR & D systems, Minneapolis) for one hour at 20° C. Excess antibody was removed by washing with PBS and 0.5% NONIDET P40 (Sigma) and was followed by incubation with 1/100 dilution of HRP-conjugated goat anti-rabbit IgG (Sigma) for one hour at 20° C. (The word NONIDET is a trade mark). The nitrocellulose sheets were finally washed with PBS and 0.5% NP40, followed by washing with PBS alone. The blots were developed with 0.05% diaminobenzidine and 0.03% hydrogen peroxide.

N-terminal sequencing

N-terminal sequence dam was obtained with a 471A Applied Biosystems pulsed liquid sequenator with a liquid chromatography system modified to use a 140A solvent delivery system. 8 μg PDGF-BB, BS, B7 or B44 in 0.1% (v/v) trifluoroacetic acid or 10 mM acetic acid were subjected 10–12 cycles of automated Edman degradation. The amino acids detected were aligned with the PDGF-B sequence and the percentage of each N-terminal amino acid calculated. Internal cleavage at Thr33 was expressed as the percentage of total PDGF, independent of the small mount of N-terminal processing from Serl-Thr6.

Cell Culture

Swiss 3T3 cells were maintained in Dulbecco's Modified Eagle's Medium (DMEM) supplemented with 10% (v/v) foetal calf serum (FCS) at 37° C. in a humidified atmosphere of 5% $CO_2$/95% air. Cultures were routinely monitored for spontaneous transformants.

Mitogenesis Assay

The uptake of [$^3$H]thymidine by Swiss 3T3 cells was used as a measure of DNA synthesis. Cells were seeded into microtitre plates (Falcon) at a density of $1\times10^4$ per well with DMEM containing 10% FCS. After incubation at 37° C. for 6–8 days, when the cells were confluent and quiescent, diluted test samples (yeast supernatant or purified material) were added directly to the wells. The plates were incubated for 16 hours at 37° C. before pulsing with [$^3$H]thymidine (1 μCi/ml) for 6 hours. Incorporation of [$^3$H]thymidine into trichloroacetic acid-insoluble material was determined as described by Raine and Ross, (1985) *Methods. Enzymol*, 109, 749–773. PDGF activity of the test samples was quantified by interpolation from the dose response curve for a PDGF-BB standard c-sis (Amersham).

Phosphoinositol Turnover Assay

Swiss 3T3 cells were seeded into 24 well tissue culture plates (Falcon) at $1\times10^5$ per well. After 3 days, the cells were pre-labelled for a period of 72 hours by adding [$^3$H]myo-inositol at 3 mcCi/ml directly to the growth medium. The monolayers were rinsed and subsequently incubated for 20 minutes at 37° C. with 0.5 ml per well of Hank's Balanced Salt Solution (HBSS) containing 10 mM $LiCl_2$ to inactivate inositol-1-phosphatase (Berridge, Downes & Hanley, (1982) *Biochem. J.*, 206, 587–595). Dilutions of the samples and PDGF standard (c-sis made up at 25 times the desired concentration) were added to the wells and incubated at 37° C. for 20 minutes. Controls, such as yeast supernatant without PDGF, were included for comparison.

The reaction was stopped by aspiration of the medium and addition of 1 ml ice-cold 5% (v/v) perchloric acid per well. The plates were kept on ice for 30 minutes to extract the cellular inositol phosphates. Precipitated cellular protein was removed by centrifugation and perchloric acid quantitatively removed from the supernatant solution by the method of Khym, (1975), *Clin. Chem.*, 21, 1245–1252. Samples of the neutralised cell extracts (0.7 ml) were diluted to 5 ml with 5 mM potassium tetraborate/0.5 mM EDTA. The accumulated labelled inositol monophosphates were separated by the method of Bone, Fretten, Palmer, Kirk & Michell, (1984) *Biochem. J.*, 221, 803–811 using AG 1-X8 anion exchange resin (Bio-Rad). Column fractions were mixed with OPTIPHASE scintillant (LKB) and the level of radioactivity determined for each fraction (Beckman LS 5000CE). (The word OPTIPHASE is a trade mark.)

Solid Phase Sandwich ELISA

This assay was developed using two antibodies to PDGF: goat anti-human PDGF-AB (Collaborative Research) and rabbit anti-human PDGF-BB (Genzyme). All washes and dilutions were made using 0.05% (v/v) TWEEN 20 (Sigma)/PBS, unless stated otherwise. (The word TWEEN is a trade mark). A 96-well immunoplate (Nunc-Maxisorp) was coated overnight at 4° C. with goat anti-PDGF antibody at 5 μg/ml in 0.05M sodium carbonate/bicarbonate buffer, pH 9.6. Remaining protein adsorption sites were blocked by incubation with 0.1% w/v casein/PBS for 30 minutes at 20° C. and the plate was washed 3 times. Serial dilutions of the test samples and PDGF standard (c-sis, Amenham) were made by titration access the sensitised plate in PBSfTween. The plate was incubated for 1 hour at 200° C. After washing 3 times, 50 µl rabbit anti-PDGF antibody (5 µg/ml) was added to each well and incubated for 1 hour at 20° C. The plate was washed a further 3 times followed by addition of HRP-conjugated goat anti-rabbit IgG (Tago), at a dilution of 1/1000, for 1 hours at 20° C. After 5 washes, the chromogenic peroxidase substrate tetramethylbenzidine (TMB) was added at 100 µg/ml in 0.1M citric acid with 0.04% (v/v) hydrogen peroxide. When sufficient colour had developed (typically 5–15 minutes), the reaction was stopped by addition of 2.5M $H_2SO_4$ and the absorbance was read at 450 nm (Dynatech MR650 plate reader).

Competition ELISA

All washes and dilutions were made using 0.05% (v/v) Tween 20 (Sigma)/PBS. unless stated otherwise. A 96 well immunoplate (Nunc-Maxisorp) plates was coated with 100 µl per well of PDGF at 20 ng/ml in PBS, and incubated overnight at 4° C. Remaining protein adsorption sites were blocked by incubation with 0.1% (w/v) casein/PBS for 1 hour at 20° C. and the plate was washed 3 times. In a separate v-well titertek plate PDGF standard and samples were diluted in 2 fold serial dilutions at a final volume of 60 µl in pBS/Tween. Rabbit anti human PDGF (Genzyme anti PDGF-B or R and D Systems anti PDGF-AB) antibody, 60 µl at 1/100 dilution (10 µg/ml), was added and incubated for 1 hour at 20° C. 100 µl was transferred to the PDGF coated and blocked plate and incubated for 1 hour. The plate was washed a further 3 times followed followed by addition of HRP-conjugated goat anti-rabbit IgG Crago), at a dilution of 1/1000, for 1 hour at 20° C. After 5 washes, the chromogenic peroxidase substrate tetramethylbenzidine (TMB) was added at 100 µg/ml in 0.1M sodium acetate buffered to pH 6.0 with 0.1 citric acid with 0.04% (v/v) hydrogen peroxide. When sufficient colour had developed (typically 5–15 minutes), the reaction was stopped by addition of 2.5M H2SO4 and the absorbance was read at 450 nm (Dynatech Mr650 plate reader).

Results

The levels of expression of the PDGF products of Examples 1 to 3 and Comparative Examples A-D in the culture medium are shown in Table 1.

Table 1 shows expression levels of full length PDGF-B, PDGF-Bt (Comparative Examples A and B) and the mutants PDGF-B5, PDGF-B7 and PDGF-B44 of Examples 1 to 3 in pSW6. Yeast expressing PDGF-B was grown for six days following induction and the supernatants assayed by ELISA, PI and mitogenesis.

It can be seen that the variants of Examples 1 to 3 are expressed at about 5 to 10 times the level of the naturally occurring PDGF-B and the truncated PDGF-B of the comparative examples. Indeed, the expression levels of the naturally occurring and the truncated products were about 10 fold lower than expression levels expected from comparisons with other heterologous proteins such as epidermal growth factor and maximum levels were only observed after six to seven days following induction.

TABLE 1

| Gene | Sandwich ELISA | Mitogenesis ng/ml | PI ng/ml |
|---|---|---|---|
| PDGF-B comparative Example A | 333 | 308 | ND |
| PDGF-Bt Comparative Example B | 494 | 342 | 123 |
| PDGF-B4 Comparative Example C | 286 | 250 | 10 |
| PDGF-B6 Comparative Example D | 32 | 54 | ND |
| PDGF-B5 Example 1 | 2720 | 1612 | 940 |
| PDGF-B7 Example 2 | 2965 | 2015 | >3000 |
| PDGF-B44 Example 3 | 6093* | 4334 | 6720 |

*Competition ELISA ng/ml

To determine at what level expression of PDGF-B was being limited, the plasmid copy number, transcript levels, and the intra and extra-cellular concentrations of PDGF-B following induction were determined. For Comparative Examples A and B copy numbers were determined and found to be, as expected, around 200 copies per cell. In addition, PDGF-B mRNA levels 16 hours after transfer to galactose showed the expected induction of PDGF transcripts (see FIG. 4). Soluble intra-cellular levels of PDGF-B were detected one day following induction at approximately 600 ng/ml and remained high over the six days. However, it took six days for significant accumulation of PDGF-B into the medium and even at this stage there was still 2–3 times more intra-cellular PDGF-B than in the medium. At no time was any significant level (>4 ng/ml) of PDGF-B found in the cell wall of yeast which indicates that the majority of PDGF-B found in the culture medium is derived from limited cell lysis rather than true secretion. Thus a major limiting factor to PDGF-B expression in yeast is the secretion of PDGF-B into the medium.

Protease resistant mutants

As can be seen from Table 1, the PDGF-B variants of Examples 1 to 3 all expressed PDGF-B at levels 5–10 fold higher than the wild-type molecule. Analysis of the PDGF-B levels following induction revealed high intracellular levels (400–1500ng/ml) for the mutants but over the six days, a much higher proportion of PDGF-B was detected accumulating in the medium than with the naturally occurring or the truncated product.

The results of the analysis by SDS-PAGE of the PDGF-BB products of the examples and comparative examples are shown in FIG. 5. Truncated PDGF-BB appears as a single diffuse band of molecular weight 28000 under non-reducing conditions. This is larger than expected; the calculated molecular weight is 24,600.

This discrepancy is thought to be due to glycosylation of the molecules. Under reducing conditions, two bands of approximate molecular weights 14000 and 10000 are apparent. As can be seen from Table 2, N-terminal sequencing of naturally occurring PDGF-BB shows that 50% of the molecules are cleaved after arginine 32. The calculated Mr for the truncated PDGF-BB of Comparative Example B is 12300 and for the cleaved molecule is 8700. A similar analysis of the protease-resistant mutants of Examples 1 and 2 by SDS-PAGE showed a single band in both reducing and in non-reducing conditions (see FIG. 5) N-terminal sequencing indicates a low level of cleavage (approximately 10%) of the mutant PDGF-B5 of Example 1 after arginine 32. Replacement of arginine 32 with a proline residue in the mutant of PDGF-B7 of Example 2 prevents cleavage at this site and no cleavage is detected at the potential KEX2 site (arginine 27, arginine 28) by N-terminal) sequencing (see Table 2).

TABLE 2

Internal Cleavage of PDGF-B on Expression in Yeast

| Molecule of Example | % cleavage at Arg 32-Thr 33 |
|---|---|
| B (Comparative) | 49 |
| 1 (Arg 28 > Ser) | 10 |
| 2 (Arg 31 > Pro) | 0 |
| 3 (Arg 28 > Ser, Arg 32 > Pro) | 0 |

In yeast the product of the KEX2 gene is required for the proteolytic processing of the alpha-factor mating pheromone and the killer toxin precursors. The protein is a membrane bound calcium-dependent endopeptidase located in the golgi and cleaves on the carboxyl side of a pair of basic residues.

From Table 2 it can be seen that protease cleavage after arginine 32 is found in almost 50% of the wild type PDGF-B isolated. It is not clear if the KEX2 product is responsible for this cleavage as this site does not contain a pair of basic residues. However, it has been observed that KEX2 can exhibit cleavage at sites other than dibasic residues. The mutation of Example 1 disrupts a potential EX2 site in PDGF-B at position 27-28 but reduces cleavage after arginine 32 to 10%. It seems likely that the mutation of Example 1 in which arginine 28 is replaced by serine reduces the accessibility of a protease to the cleavage site at arginine 32. The molecules of Examples 1 and 2 both have similar secondary structures to the wild-type molecule and so structural change does not appear to be responsible for changing the cleavage specifically.

TABLE 3

Biological activity of PDGF-BB

| PDGF-BB Dimer of Product of Examples | Protein Level (µg/ml) | Mitogenic Activity (µg/ml) | PI Turnover (µg/ml) | ELISA (µg/ml) |
|---|---|---|---|---|
| B | 100 | 55 | 76 | 263 |
| 1 | 100 | 130 | 203 | 247 |
| 2 | 100 | 131 | 266 | 297 |
| 3 | 100 | 125 | 282 | 208 |

In addition to their other advantages, it has been found that the mutants of Examples 1 and 2 show increased specific activity compared to wild-type PDGF-BB. This difference is illustrated in Table 3 and may be related to the cleavage of wild-type PDGF-BB in the receptor binding region which occurs between isoleucine 25 and phenylalanine 37. Since 50% of the PDGF-B molecules are cleaved in this region, then only the remaining 50% could be expected to show any biological activity.

It can therefore be seen that the mutations exemplified in Examples 1 to 3 are extremely effective in increasing the yield of PDGF-B from expression in yeast. In addition, the mutants are biologically active and in fact show a greater degree of activity than the naturally-occurring molecule.

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
        ( A ) LENGTH: 160 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..160
        ( D ) OTHER INFORMATION: /note="PDGF-B"

( x i ) SEQUENCE DESCRIPTION: SEQ ID NO:1:

```
Ser  Leu  Gly  Ser  Leu  Thr  Ile  Ala  Glu  Pro  Ala  Met  Ile  Ala  Glu  Cys
 1              5                        10                       15

Lys  Thr  Arg  Thr  Glu  Val  Phe  Glu  Ile  Ser  Arg  Arg  Leu  Ile  Asp  Arg
              20                        25                       30

Thr  Asn  Ala  Asn  Phe  Leu  Val  Trp  Pro  Pro  Cys  Val  Glu  Val  Gln  Arg
         35                        40                  45

Cys  Ser  Gly  Cys  Cys  Asn  Asn  Arg  Asn  Val  Gln  Cys  Arg  Pro  Thr  Gln
     50                        55                  60

Val  Gln  Leu  Arg  Pro  Val  Gln  Val  Arg  Lys  Ile  Glu  Ile  Val  Arg  Lys
```

|          |     |     |     |     |     |     |     |     |     |     |     |     |     |     |     |
|----------|-----|-----|-----|-----|-----|-----|-----|-----|-----|-----|-----|-----|-----|-----|-----|
| 65       |     |     |     | 70  |     |     |     | 75  |     |     |     | 80  |     |     |

```
Lys  Pro  Ile  Phe  Lys  Lys  Ala  Thr  Val  Thr  Leu  Glu  Asp  His  Leu  Ala
               85                      90                      95

Cys  Lys  Cys  Glu  Thr  Val  Ala  Ala  Ala  Arg  Pro  Val  Thr  Arg  Ser  Pro
              100                     105                     110

Gly  Gly  Ser  Gln  Glu  Gln  Arg  Ala  Lys  Thr  Pro  Gln  Thr  Arg  Val  Thr
              115                     120                     125

Ile  Arg  Thr  Val  Arg  Val  Arg  Pro  Pro  Lys  Gly  Lys  His  Arg  Lys
     130                     135                     140

Phe  Lys  His  Thr  His  Asp  Lys  Thr  Ala  Leu  Lys  Glu  Thr  Leu  Gly  Ala
145                      150                     155                      160
```

( 2 ) INFORMATION FOR SEQ ID NO:2:

( i ) SEQUENCE CHARACTERISTICS:
    ( A ) LENGTH: 109 amino acids
    ( B ) TYPE: amino acid
    ( C ) STRANDEDNESS: single
    ( D ) TOPOLOGY: linear ( i i ) MOLECULE TYPE: protein ( i x ) FEATURE:
    ( A ) NAME/KEY: Protein
    ( B ) LOCATION: 1..109
    ( D ) OTHER INFORMATION: /note="Truncated PDGF-B (PDGF-Bt)"

( x i ) SEQUENCE DESCRIPTION: SEQ ID NO:2:

```
Ser  Leu  Gly  Ser  Leu  Thr  Ile  Ala  Glu  Pro  Ala  Met  Ile  Ala  Glu  Cys
1                    5                      10                      15

Lys  Thr  Arg  Thr  Glu  Val  Phe  Glu  Ile  Ser  Arg  Arg  Leu  Ile  Asp  Arg
               20                      25                      30

Thr  Asn  Ala  Asn  Phe  Leu  Val  Trp  Pro  Pro  Cys  Val  Glu  Val  Gln  Arg
               35                      40                      45

Cys  Ser  Gly  Cys  Cys  Asn  Asn  Arg  Asn  Val  Gln  Cys  Arg  Pro  Thr  Gln
     50                       55                      60

Val  Gln  Leu  Arg  Pro  Val  Gln  Val  Arg  Lys  Ile  Glu  Ile  Val  Arg  Lys
65                        70                      75                      80

Lys  Pro  Ile  Phe  Lys  Lys  Ala  Thr  Val  Thr  Leu  Glu  Asp  His  Leu  Ala
               85                      90                      95

Cys  Lys  Cys  Glu  Thr  Val  Ala  Ala  Ala  Arg  Pro  Val  Thr
              100                     105
```

( 2 ) INFORMATION FOR SEQ ID NO:3:

( i ) SEQUENCE CHARACTERISTICS:
    ( A ) LENGTH: 109 amino acids
    ( B ) TYPE: amino acid
    ( C ) STRANDEDNESS: single
    ( D ) TOPOLOGY: linear ( i i ) MOLECULE TYPE: protein ( i x ) FEATURE:
    ( A ) NAME/KEY: Protein
    ( B ) LOCATION: 1..109
    ( D ) OTHER INFORMATION: /note="Truncated PDGF-B with ARG
            28 SER (PDGF-B5)"

( x i ) SEQUENCE DESCRIPTION: SEQ ID NO:3:

```
Ser  Leu  Gly  Ser  Leu  Thr  Ile  Ala  Glu  Pro  Ala  Met  Ile  Ala  Glu  Cys
1                    5                      10                      15

Lys  Thr  Arg  Thr  Glu  Val  Phe  Glu  Ile  Ser  Arg  Ser  Leu  Ile  Asp  Arg
               20                      25                      30
```

```
Thr  Asn  Ala  Asn  Phe  Leu  Val  Trp  Pro  Pro  Cys  Val  Glu  Val  Gln  Arg
          35                       40                      45

Cys  Ser  Gly  Cys  Cys  Asn  Asn  Arg  Asn  Val  Gln  Cys  Arg  Pro  Thr  Gln
     50                       55                      60

Val  Gln  Leu  Arg  Pro  Val  Gln  Val  Arg  Lys  Ile  Glu  Ile  Val  Arg  Lys
65                       70                      75                          80

Lys  Pro  Ile  Phe  Lys  Lys  Ala  Thr  Val  Thr  Leu  Glu  Asp  His  Leu  Ala
               85                        90                           95

Cys  Lys  Cys  Glu  Thr  Val  Ala  Ala  Ala  Arg  Pro  Val  Thr
               100                 105
```

(2) INFORMATION FOR SEQ ID NO:4:

(i) SEQUENCE CHARACTERISTICS:
        (A) LENGTH: 109 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..109
        (D) OTHER INFORMATION: /note="Truncated PDGF-B with ARG
            32 PRO (PDGF-B7)"

(xi) SEQUENCE DESCRIPTION: SEQ ID NO:4:

```
Ser  Leu  Gly  Ser  Leu  Thr  Ile  Ala  Glu  Pro  Ala  Met  Ile  Ala  Glu  Cys
1                    5                        10                          15

Lys  Thr  Arg  Thr  Glu  Val  Phe  Glu  Ile  Ser  Arg  Arg  Leu  Ile  Asp  Pro
               20                       25                      30

Thr  Asn  Ala  Asn  Phe  Leu  Val  Trp  Pro  Pro  Cys  Val  Glu  Val  Gln  Arg
          35                       40                      45

Cys  Ser  Gly  Cys  Cys  Asn  Asn  Arg  Asn  Val  Gln  Cys  Arg  Pro  Thr  Gln
     50                       55                      60

Val  Gln  Leu  Arg  Pro  Val  Gln  Val  Arg  Lys  Ile  Glu  Ile  Val  Arg  Lys
65                       70                      75                          80

Lys  Pro  Ile  Phe  Lys  Lys  Ala  Thr  Val  Thr  Leu  Glu  Asp  His  Leu  Ala
               85                        90                           95

Cys  Lys  Cys  Glu  Thr  Val  Ala  Ala  Ala  Arg  Pro  Val  Thr
               100                 105
```

(2) INFORMATION FOR SEQ ID NO:5:

(i) SEQUENCE CHARACTERISTICS:
        (A) LENGTH: 109 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..109
        (D) OTHER INFORMATION: /note="Truncated PDGF-B with Arg
            28 Ser and Arg 32 Pro (PDGF-B44)"

(xi) SEQUENCE DESCRIPTION: SEQ ID NO:5:

```
Ser  Leu  Gly  Ser  Leu  Thr  Ile  Ala  Glu  Pro  Ala  Met  Ile  Ala  Glu  Cys
1                    5                        10                          15

Lys  Thr  Arg  Thr  Glu  Val  Phe  Glu  Ile  Ser  Arg  Ser  Leu  Ile  Asp  Pro
               20                       25                      30
```

|     |     |     |     |     |     |     |     |     |     |     |     |     |     |     |
| --- | --- | --- | --- | --- | --- | --- | --- | --- | --- | --- | --- | --- | --- | --- |
| Thr | Asn | Ala 35 | Asn | Phe | Leu | Val | Trp 40 | Pro | Pro | Cys | Val | Glu 45 | Val | Gln | Arg |
| Cys | Ser | Gly 50 | Cys | Cys | Asn | Asn 55 | Arg | Asn | Val | Gln | Cys 60 | Arg | Pro | Thr | Gln |
| Val 65 | Gln | Leu | Arg | Pro | Val 70 | Gln | Val | Arg | Lys 75 | Ile | Glu | Ile | Val | Arg | Lys 80 |
| Lys | Pro | Ile | Phe | Lys 85 | Lys | Ala | Thr | Val | Thr 90 | Leu | Glu | Asp | His | Leu 95 | Ala |
| Cys | Lys | Cys | Glu 100 | Thr | Val | Ala | Ala | Ala 105 | Arg | Pro | Val | Thr |

( 2 ) INFORMATION FOR SEQ ID NO:6:

( i ) SEQUENCE CHARACTERISTICS:
        ( A ) LENGTH: 514 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..514
        ( D ) OTHER INFORMATION: /note="Synthetic PDGF-B gene"

( x i ) SEQUENCE DESCRIPTION: SEQ ID NO:6:

```
AAGCTTACCT GCTATGTCCT TGGGTTCGTT AACCATCGCT GAACCGGCTA TGATCGCCGA      60
ATGTAAGACG CGTACCGAAG TTTTCGAAAT CTCGAGACGT TTGATTGACC GCACCAACGC     120
CAACTTCCTG GTTTGGCCGC CATGTGTTGA AGTCCAACGC TGCAGTGGTT GCTGTAACAA     180
CAGAAACGTT CAGTGTCGAC CTACTCAGGT TCAACTGCGT CCTGTCCAAG TTCGTAAGAT     240
CGAAATTGTA CGTAAGAAAC CAATCTTCAA GAAAGCCACT GTAACTCTAG AAGACCACCT     300
GGCATGCAAG TGTGAAACTG TTGCAGCTGC TCGCCCTGTT ACTAGATCTC CGGGTGGTTC     360
CCAGGAACAA CGCGCTAAAA CCCCACAAAC CCGGGTTACC ATCAGAACTG TTCGCGTCCG     420
TAGACCTCCC AAGGGTAAAC ACCGCAAATT CAAGCACACC CACGACAAAA CCGCTTTAAA     480
GGAAACCTTA GGTGCTTAGT AAGGATCCGA ATTC                                 514
```

( 2 ) INFORMATION FOR SEQ ID NO:7:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..19
        ( D ) OTHER INFORMATION: /note="Primer complementary to
            universal primer region of pUC18"

( x i ) SEQUENCE DESCRIPTION: SEQ ID NO:7:

```
CAGGGTTTTC CCAGTCACG                                                   19
```

( 2 ) INFORMATION FOR SEQ ID NO:8:

( i ) SEQUENCE CHARACTERISTICS:
        ( A ) LENGTH: 29 base pairs
        ( B ) TYPE: nucleic acid
        ( C ) STRANDEDNESS: single (D) TOPOLOGY: linear (ii) MOLECULE TYPE: cDNA (ix) FEATURE:
    (A) NAME/KEY: misc_feature
    (B) LOCATION: 1..29
    (D) OTHER INFORMATION: /note="Oligo DNA 3'portion complimentary to Seq Id No. 9"

(xi) SEQUENCE DESCRIPTION: SEQ ID NO:8:

```
AGCTTGGATA AAAGATCCTT GGGTTCGTT                                              29
```

(2) INFORMATION FOR SEQ ID NO:9:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..25
        (D) OTHER INFORMATION: /note="Oligo complimentary to 3' region of Seq Id No. 8"

(xi) SEQUENCE DESCRIPTION: SEQ ID NO:9:

```
AACGAACCCA AGGATCTTTT ATCCA                                                  25
```

(2) INFORMATION FOR SEQ ID NO:10:

(i) SEQUENCE CHARACTERISTICS:
        (A) LENGTH: 514 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..514
        (D) OTHER INFORMATION: /note="PDGF-B5 gene adapted at 5' end for fusion to alpha factor"

(xi) SEQUENCE DESCRIPTION: SEQ ID NO:10:

```
AAGCTTGGAT AAAAGATCCT TGGGTTCGTT AACCATCGCT GAACCGGCTA TGATCGCCGA    60
ATGTAAGACG CGTACCGAAG TTTTCGAAAT CTCGAGATCC TTGATTGACC GCACCAACGC   120
CAACTTCCTG GTTTGGCCGC CATGTGTTGA AGTCCAACGC TGCAGTGGTT GCTGTAACAA   180
CAGAAACGTT CAGTGTCGAC CTACTCAGGT TCAACTGCGT CCTGTCCAAG TTCGTAAGAT   240
CGAAATTGTA CGTAAGAAAC CAATCTTCAA GAAAGCCACT GTAACTCTAG AAGACCACCT   300
GGCATGCAAG TGTGAAACTG TTGCAGCTGC TCGCCCTGTT ACTTAGTAAG GATCCGAATT   360
CCAGGAACAA CGCGCTAAAA CCCCACAAAC CCGGGTTACC ATCAGAACTG TTCGCGTCCG   420
TAGACCTCCC AAGGGTAAAC ACCGCAAATT CAAGCACACC CACGACAAAA CCGCTTTAAA   480
GGAAACCTTA GGTGCTTAGT AAGGATCCGA ATTC                              514
```

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear ( i i ) MOLECULE TYPE: cDNA ( i x ) FEATURE:
    ( A ) NAME/KEY: misc_feature
    ( B ) LOCATION: 1..20
    ( D ) OTHER INFORMATION: /note="Synthetic oligonucleotide"

( x i ) SEQUENCE DESCRIPTION: SEQ ID NO:11:

```
ATCCTTACTA AGTAACAGGG                                                                           20
```

( 2 ) INFORMATION FOR SEQ ID NO:12:

( i ) SEQUENCE CHARACTERISTICS:
        ( A ) LENGTH: 361 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
    ( A ) NAME/KEY: misc_feature
    ( B ) LOCATION: 1..361
    ( D ) OTHER INFORMATION: /note="PDGF-B gene adapted at 5'
        end for fusion to alpha factor and truncated at 3'
        end to remove C-terminal coding residues"

( x i ) SEQUENCE DESCRIPTION: SEQ ID NO:12:

```
AAGCTTGGAT AAAAGATCCT TGGGTTCGTT AACCATCGCT GAACCGGCTA TGATCGCCGA        60
ATGTAAGACG CGTACCGAAG TTTTCGAAAT CTCGAGACGT TGATTGACC  GCACCAACGC       120
CAACTTCCTG GTTTGGCCGC CATGTGTTGA AGTCCAACGC TGCAGTGGTT GCTGTAACAA       180
CAGAAACGTT CAGTGTCGAC CTACTCAGGT TCAACTGCGT CCTGTCCAAG TTCGTAAGAT       240
CGAAATTGTA CGTAAGAAAC CAATCTTCAA GAAAGCCACT GTAACTCTAG AAGACCACCT       300
GGCATGCAAG TGTGAAACTG TTGCAGCTGC TCGCCCTGTT ACTTAGTAAG GATCCGAATT       360
C                                                                      361
```

( 2 ) INFORMATION FOR SEQ ID NO:13:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
    ( A ) NAME/KEY: misc_feature
    ( B ) LOCATION: 1..40
    ( D ) OTHER INFORMATION: /note="probe for PDGF transcripts"

( x i ) SEQUENCE DESCRIPTION: SEQ ID NO:13:

```
CGAGATTTCG AAAACTTCGG TACGCGTCTT ACATTCGGCG                                                     40
```

( 2 ) INFORMATION FOR SEQ ID NO:14:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
    ( A ) NAME/KEY: misc_feature
    ( B ) LOCATION: 1..30

( D ) OTHER INFORMATION: /note="probe for yeast 18s ribosomal RNA"

( x i ) SEQUENCE DESCRIPTION: SEQ ID NO:14:

TGATCCTTCC GCAGGTTCAC CTACGGAAAC   30

( 2 ) INFORMATION FOR SEQ ID NO:15:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..19
        ( D ) OTHER INFORMATION: /note="Synthetic primer for PDGF-B4"

( x i ) SEQUENCE DESCRIPTION: SEQ ID NO:15:

TCAAACGTTC CGAGATTTC   19

( 2 ) INFORMATION FOR SEQ ID NO:16:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..19
        ( D ) OTHER INFORMATION: /note="Primer for PDGF-B6"

( x i ) SEQUENCE DESCRIPTION: SEQ ID NO:16:

TTGGTGCGCT TAATCAAAC   19

( 2 ) INFORMATION FOR SEQ ID NO:17:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..19
        ( D ) OTHER INFORMATION: /note="primer for PDGF-B5"

( x i ) SEQUENCE DESCRIPTION: SEQ ID NO:17:

CAATCAAGGA TCTCGAGAT   19

( 2 ) INFORMATION FOR SEQ ID NO:18:

( i ) SEQUENCE CHARACTERISTICS:
        ( A ) LENGTH: 361 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:

(A) NAME/KEY: misc_feature
(B) LOCATION: 1..361
(D) OTHER INFORMATION: /note="synthetic PDGF-B5 gene"

(xi) SEQUENCE DESCRIPTION: SEQ ID NO:18:

| | | | | | | |
|---|---|---|---|---|---|---|
| AAGCTTGGAT | AAAAGATCCT | TGGGTTCGTT | AACCATCGCT | GAACCGGCTA | TGATCGCCGA | 60 |
| ATGTAAGACG | CGTACCGAAG | TTTTCGAAAT | CTCGAGATCC | TTGATTGACC | GCACCAACGC | 120 |
| CAACTTCCGC | GTTTGGCCGC | CATGTGTTGA | AGTCCAACGC | TGCAGTGGTT | GCTGTAACAA | 180 |
| CAGAAACGTT | CAGTGTCGAC | CTACTCAGGT | TCAACTGCGT | CCTGTCCAAG | TTCGTAAGAT | 240 |
| CGAAATTGTA | CGTAAGAAAC | CAATCTTCAA | GAAAGCCACT | GTAACTCTAG | AAGACCACCT | 300 |
| GGCATGCAAG | TGTGAAACTG | TTGCAGCTGC | TCGCCCTGTT | ACTTAGTAAG | GATCCGAATT | 360 |
| C | | | | | | 361 |

(2) INFORMATION FOR SEQ ID NO:19:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: misc_feature
(B) LOCATION: 1..18
(D) OTHER INFORMATION: /note="primer PDGF-B7 gene"

(xi) SEQUENCE DESCRIPTION: SEQ ID NO:19:

GCGTTGGTTG GGTCAATC    18

(2) INFORMATION FOR SEQ ID NO:20:

(i) SEQUENCE CHARACTERISTICS:
(A) LENGTH: 361 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: misc_feature
(B) LOCATION: 1..361
(D) OTHER INFORMATION: /note="synthetic PDGF-B7 gene"

(xi) SEQUENCE DESCRIPTION: SEQ ID NO:20:

| | | | | | | |
|---|---|---|---|---|---|---|
| AAGCTTGGAT | AAAAGATCCT | TGGGTTCGTT | AACCATCGCT | GAACCGGCTA | TGATCGCCGA | 60 |
| ATGTAAGACG | CGTACCGAAG | TTTTCGAAAT | CTCGAGACGT | TTGATTGACC | CAACCAACGC | 120 |
| CAACTTCCTG | GTTTGGCCGC | CATGTGTTGA | AGTCCAACGC | TGCAGTGGTT | GCTGTAACAA | 180 |
| CAGAAACGTT | CAGTGTCGAC | CTACTCAGGT | TCAACTGCGT | CCTGTCCAAG | TTCGTAAGAT | 240 |
| CGAAATTGTA | CGTAAGAAAC | CAATCTTCAA | GAAAGCCACT | GTAACTCTAG | AAGACCACCT | 300 |
| GGCATGCAAG | TGTGAAACTG | TTGCAGCTGC | TCGCCCTGTT | ACTTAGTAAG | GATCCGAATT | 360 |
| C | | | | | | 361 |

(2) INFORMATION FOR SEQ ID NO:21:

(i) SEQUENCE CHARACTERISTICS:
(A) LENGTH: 18 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:21:

GCGTTGGTTG GGTCAATC                                                                                              1 8

(2) INFORMATION FOR SEQ ID NO:22:

(i) SEQUENCE CHARACTERISTICS:
  (A) LENGTH: 361 base pairs
  (B) TYPE: nucleic acid
  (C) STRANDEDNESS: single
  (D) TOPOLOGY: linear (i i) MOLECULE TYPE: cDNA (i x) FEATURE:
  (A) NAME/KEY: misc_feature
  (B) LOCATION: 1..361
  (D) OTHER INFORMATION: /note="PDGF-B44 gene"

(x i) SEQUENCE DESCRIPTION: SEQ ID NO:22:

| | | | | | |
|---|---|---|---|---|---|
| AAGCTTGGAT | AAAAGATCCT | TGGGTTCGTT | AACCATGCT | GAACCGGCTA | TGATCGCCGA | 6 0 |
| ATGTAAGACG | CGTACCGAAG | TTTTCGAAAT | CTCGAGATCC | TTGATTGACC | CAACCAACGC | 1 2 0 |
| CAACTTCCTG | GTTTGGCCGC | CATGTGTTGA | AGTCCAACGC | TGCAGTGGTT | GCTGTAACAA | 1 8 0 |
| CAGAAACGTT | CAGTGTCGAC | CTACTCAGGT | TCAACTGCGT | CCTGTCCAAG | TTCGTAAGAT | 2 4 0 |
| CGAAATTGTA | CGTAAGAAAC | CAATCTTCAA | GAAAGCCACT | GTAACTCTAG | AAGACCACCT | 3 0 0 |
| GGCATGCAAG | TGTGAAACTG | TTGCAGCTGC | TCGCCCTGTT | ACTTAGTAAG | GATCCGAATT | 3 6 0 |
| C | | | | | | 3 6 1 |

We claim:

1. A PDGF-B analogue wherein Arg 28 and/or Arg 32 of a naturally occurring PDGF-B chain is replaced with an amino acid residue which reduces or prevents protease cleavage of said analogue on expression in yeast.

2. A PDGF-B analogue as claimed in claim 1 wherein Arg 28 is replaced by a non-basic amino acid residue.

3. A PDGF-B analogue as claimed in claim 2 wherein Arg 28 is replaced by a non-basic amino acid residue.

4. A PDGF-B analogue as claimed in claim 3 wherein Arg 28 is replaced by Ser.

5. A PDGF-B analogue as claimed in claim 1, wherein Arg 32 is replaced by a non-basic amino acid residue.

6. A PDGF-B analogue as claimed in claim 1, wherein Arg 32 is replaced by a non-basic non-polar amino acid residue.

7. A PDGF-B analogue as claimed in claim 6, wherein Arg 32 is replaced by Pro.

8. A PDGF-B analogue as claimed in claim 1 wherein Arg 28 is replaced by Ser and Arg 32 is replaced by Pro.

9. A pharmaceutical composition containing at least one PDGF dimer comprising at least one PDGF-B analogue as claimed in claim 1 together with a pharmaceutically or veterinary acceptable carrier therefor.

10. A pharmaceutical composition as claimed in claim 9 which is adapted for parenteral, buccal, dermal or transdermal administration.

11. A PDGF-B analogue having the amino acid sequence of SEQ ID NO: 3.

12. A PDGF-B analogue having the amino acid sequence of SEQ ID NO: 4.

13. A PDGF-B analogue having the amino acid sequence of SEQ ID NO: 5.

14. A recombinant or isolated nucleic acid sequence coding for a PDGF-B analogue wherein Arg 28 and/or Arg 32 of a naturally occurring PDGF-B chain is replaced by an amino acid residue which reduces or prevents protease cleavage of said analogue on expression in yeast.

15. A recombinant or isolated nucleic acid sequence according to claim 14, wherein said sequence has a codon usage optimized for E. coli or yeast.

16. A recombinant or isolated nucleic acid sequence according to claim 15, wherein said sequence has a codon usage optimized for yeast.

17. A vector comprising the recombinant nucleic acid sequence as claimed in claim 14.

18. A vector as claimed in claim 17 which is a plasmid, a cosmid or a phage.

19. A vector as claimed in claim 17 which is a cloning vector.

20. A vector as claimed in claim 17 which is an expression vector.

21. A host cell comprising a vector containing DNA encoding a PDGF-B analogue wherein Arg 28 and/or Arg 32 of a naturally occurring PDGF-B chain is replaced by an amino acid residue which reduces or prevents protease cleavage of said analogue on expression in yeast.

22. A host cell as claimed in claim 21 which is E. coli.

23. A host cell as claimed in claim 21 which is a yeast.

24. A method for increasing the yield of PDGF-B analogue expression in a yeast cell comprising:

(a) transforming a yeast cell with a DNA sequence encoding a PDGF-B analogue wherein Arg 28 and/or Arg 32 of a naturally occurring PDGF-B chain is replaced with an amino acid residue which reduces or prevents protease cleavage of said analogue on expression in said yeast cell; and (b) cultivating the transformed yeast cell for a time and under conditions suitable for expression of PDGF-B.

25. A method for preparing a PDGF-AB heterodimer comprising the steps of:

(a) transforming a yeast cell with DNA sequences encoding a PDGF-A chain and a PDGF-B analogue wherein Arg 28 and/or Arg 32 of a naturally occurring PDGF-B chain is replaced with an amino acid residue which reduces or prevents protease cleavage of said analogue on expression in yeast;

(b) cultivating said transformed yeast cell for a time and under conditions sufficient to co-express the PDGF-A chain and PDGF-B analogue encoded by said DNA sequences and allow said PDGF-A chain and PDGF-B analogue to form said PDGF-AB heterodimer; and (c) recovering the PDGF-AB heterodimer.

26. A method as claimed in claim 25 wherein said DNA sequences are contained in a vector.

* * * * *